US010238747B2

(12) United States Patent
Zimmerman

(10) Patent No.: US 10,238,747 B2
(45) Date of Patent: Mar. 26, 2019

(54) METHOD FOR INDUCING AN IMMUNE RESPONSE AGAINST AVIAN, SWINE, SPANISH, H1N1, H5N9 INFLUENZA VIRUSES AND FORMULATIONS THEREOF

(75) Inventor: Daniel H. Zimmerman, Bethesda, MD (US)

(73) Assignee: Cel-Sci, Corp, Vienna, VA (US)

( * ) Notice: Subject to any disclaimer, the term of this patent is extended or adjusted under 35 U.S.C. 154(b) by 153 days.

(21) Appl. No.: 13/994,092

(22) PCT Filed: Dec. 13, 2011

(86) PCT No.: PCT/US2011/064746
§ 371 (c)(1), (2), (4) Date: Jun. 13, 2013

(87) PCT Pub. No.: WO2012/082803
PCT Pub. Date: Jun. 21, 2012

(65) Prior Publication Data

US 2013/0266599 A1 Oct. 10, 2013

Related U.S. Application Data

(60) Provisional application No. 61/422,474, filed on Dec. 13, 2010.

(51) Int. Cl.

| | |
|---|---|
| *A61K 47/48* | (2006.01) |
| *A61K 39/12* | (2006.01) |
| *A61K 39/145* | (2006.01) |
| *A61K 45/06* | (2006.01) |
| *A61K 47/64* | (2017.01) |
| *A61K 39/00* | (2006.01) |

(52) U.S. Cl.
CPC .......... *A61K 47/4833* (2013.01); *A61K 39/12* (2013.01); *A61K 39/145* (2013.01); *A61K 45/06* (2013.01); *A61K 47/646* (2017.08); *A61K 2039/5154* (2013.01); *A61K 2039/6031* (2013.01); *A61K 2039/70* (2013.01); *C12N 2760/16134* (2013.01)

(58) Field of Classification Search
None
See application file for complete search history.

(56) References Cited

U.S. PATENT DOCUMENTS

2003/0138769 A1* 7/2003 Birkett .............................. 435/5
2004/0057968 A1* 3/2004 Zimmerman .......... A61K 39/21 424/208.1

FOREIGN PATENT DOCUMENTS

WO WO 96/22067 * 7/1996
WO WO2008043157 4/2008
WO WO2013138871 A1 9/2013

OTHER PUBLICATIONS

Taylor et al., Cellular Immunology 2010 vol. 262, pp. 1-5, online on Feb. 1, 2010.*
Benham, Citrullinated peptide dendritic cell immunotherapy in LA risk genotype—positive rheumatoid arthritis patients, Rheumatoid Arthritis, vol. 7, issue 290, pp. 1-12, 2015 year.
U.S. Appl. No. 60/853,814.

* cited by examiner

*Primary Examiner* — Shanon A. Foley
*Assistant Examiner* — Myron G Hill
(74) *Attorney, Agent, or Firm* — Roger C. Hahn; Hahn & Associates

(57) ABSTRACT

A vaccine for immunization against Type A influenza virus is provided having an immunologically effective amount of peptide constructs obtained by linking together two or more peptides based on or derived from different molecules, and methods for producing the same. The peptide constructs have the formula $P_1$-x-$P_2$ or $P_2$-x-$P_1$ where $P_1$ is associated with Type A influenza highly conserved protein such as but not limited to M2e matrix protein, NP1 nucleoprotein, HA2 core 1, and HA2 core 2, where $P_2$ is a peptide construct causing a $T_h1$ directed immune response by a set or subset of T cells to which the peptide $P_1$ is attached or that binds to a dendritic cell or T cell receptor causing said set or subset of dendritic cell or T cells to which the peptide $P_1$ is attached to initiate and complete, an immune response, and x is a direct bond or divalent linker for covalently bonding $P_1$ and $P_2$.

18 Claims, 2 Drawing Sheets

Specification includes a Sequence Listing.

```
                        SEQUENCE LISTING

<160> NUMBER OF SEQ ID NOS: 36

<210> SEQ ID NO 1
<211> LENGTH: 31
<212> TYPE: PRT
<213> ORGANISM: Artificial Sequence
<220> FEATURE:
<223> OTHER INFORMATION: synthesized peptide construct

<400> SEQUENCE: 1

Asp Leu Leu Lys Asn Gly Glu Arg Ile Glu Lys Val Glu Gly Gly Gly
1               5                   10                  15

Asn Asp Ala Thr Tyr Gln Arg Thr Arg Ala Leu Val Arg Thr Gly
            20                  25                  30

<210> SEQ ID NO 2
<211> LENGTH: 39
<212> TYPE: PRT
<213> ORGANISM: Artificial Sequence
<220> FEATURE:
<223> OTHER INFORMATION: synthesized peptide construct

<400> SEQUENCE: 2

Asp Leu Leu Lys Asn Gly Glu Arg Ile Glu Lys Val Glu Gly Gly Gly
1               5                   10                  15

Ser Leu Leu Thr Glu Val Glu Thr Pro Ile Arg Asn Glu Trp Gly Cys
            20                  25                  30

Arg Cys Asn Asp Ser Ser Asp
        35

<210> SEQ ID NO 3
<211> LENGTH: 13
<212> TYPE: PRT
<213> ORGANISM: Artificial Sequence
<220> FEATURE:
<223> OTHER INFORMATION: synthesized peptide construct

<400> SEQUENCE: 3

Asp Leu Leu Lys Asn Gly Glu Arg Ile Glu Lys Val Glu
```

```
1               5                    10
```

<210> SEQ ID NO 4
<211> LENGTH: 16
<212> TYPE: PRT
<213> ORGANISM: Artificial Sequence
<220> FEATURE:
<223> OTHER INFORMATION: synthesized peptide construct

<400> SEQUENCE: 4

```
Asp Leu Leu Lys Asn Gly Glu Arg Ile Glu Lys Val Glu Gly Gly Gly
1               5                   10                  15
```

<210> SEQ ID NO 5
<211> LENGTH: 18
<212> TYPE: PRT
<213> ORGANISM: Artificial Sequence
<220> FEATURE:
<223> OTHER INFORMATION: synthesized peptide construct

<400> SEQUENCE: 5

```
Asp Gly Gln Glu Glu Lys Ala Gly Val Val Ser Thr Gly Leu Ile Gly
1               5                   10                  15

Gly Gly
```

<210> SEQ ID NO 6
<211> LENGTH: 15
<212> TYPE: PRT
<213> ORGANISM: Artificial Sequence
<220> FEATURE:
<223> OTHER INFORMATION: synthesized peptide construct

<400> SEQUENCE: 6

```
Asp Gly Gln Glu Glu Lys Ala Gly Val Val Ser Thr Gly Leu Ile
1               5                   10                  15
```

<210> SEQ ID NO 7
<211> LENGTH: 15
<212> TYPE: PRT
<213> ORGANISM: Artificial Sequence
<220> FEATURE:
<223> OTHER INFORMATION: synthesized peptide construct

<400> SEQUENCE: 7

```
Asn Asp Ala Thr Tyr Gln Arg Thr Arg Ala Leu Val Arg Thr Gly
1               5                   10                  15
```

<210> SEQ ID NO 8
<211> LENGTH: 23
<212> TYPE: PRT
<213> ORGANISM: Artificial Sequence
<220> FEATURE:
<223> OTHER INFORMATION: synthesized peptide construct

<400> SEQUENCE: 8

```
Ser Leu Leu Thr Glu Val Glu Thr Pro Ile Arg Asn Glu Trp Gly Cys
1               5                   10                  15

Arg Cys Asn Asp Ser Ser Asp
            20
```

<210> SEQ ID NO 9
<211> LENGTH: 16
<212> TYPE: PRT
<213> ORGANISM: Artificial Sequence
<220> FEATURE:
<223> OTHER INFORMATION: synthesized peptide construct

```
<220> FEATURE:
<221> NAME/KEY: MOD_RES
<222> LOCATION: (16)..(16)
<223> OTHER INFORMATION: AMIDATION

<400> SEQUENCE: 9

Leu Lys Ser Thr Gln Asn Ala Ile Asp Glu Ile Thr Asn Lys Val Asn
1               5                   10                  15

<210> SEQ ID NO 10
<211> LENGTH: 13
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (13)..(13)
<223> OTHER INFORMATION: AMIDATION

<400> SEQUENCE: 10

Gly Leu Phe Gly Ala Ile Ala Gly Phe Ile Glu Gly Gly
1               5                   10

<210> SEQ ID NO 11
<211> LENGTH: 19
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (16)..(16)
<223> OTHER INFORMATION: AMIDATION

<400> SEQUENCE: 11

Leu Lys Ser Thr Gln Asn Ala Ile Asp Glu Ile Thr Asn Lys Val Asn
1               5                   10                  15

Gly Gly Gly

<210> SEQ ID NO 12
<211> LENGTH: 15
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (13)..(13)
<223> OTHER INFORMATION: AMIDATION

<400> SEQUENCE: 12

Gly Leu Phe Gly Ala Ile Ala Gly Phe Ile Glu Gly Gly Gly Gly
1               5                   10                  15

<210> SEQ ID NO 13
<211> LENGTH: 26
<212> TYPE: PRT
<213> ORGANISM: Artificial Sequence
<220> FEATURE:
<223> OTHER INFORMATION: synthesized peptide construct

<400> SEQUENCE: 13

Ser Leu Leu Thr Glu Val Glu Thr Pro Ile Arg Asn Glu Trp Gly Ser
1               5                   10                  15

Arg Ser Asn Asp Ser Ser Asp Gly Gly Gly
                20                  25
```

```
<210> SEQ ID NO 14
<211> LENGTH: 17
<212> TYPE: PRT
<213> ORGANISM: Artificial Sequence
<220> FEATURE:
<223> OTHER INFORMATION: synthesized peptide construct

<400> SEQUENCE: 14

Asn Asp Ala Thr Tyr Gln Arg Thr Arg Leu Val Arg Thr Gly Gly Gly
1               5                   10                  15

Gly

<210> SEQ ID NO 15
<211> LENGTH: 32
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (32)..(32)
<223> OTHER INFORMATION: AMIDATION

<400> SEQUENCE: 15

Asp Leu Leu Lys Asn Gly Glu Arg Ile Glu Lys Val Glu Gly Gly Gly
1               5                   10                  15

Leu Lys Ser Thr Gln Asn Ala Ile Asp Glu Ile Thr Asn Lys Val Asn
                20                  25                  30

<210> SEQ ID NO 16
<211> LENGTH: 29
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (29)..(29)
<223> OTHER INFORMATION: AMIDATION

<400> SEQUENCE: 16

Asp Leu Leu Lys Asn Gly Glu Arg Ile Glu Lys Val Glu Gly Gly Gly
1               5                   10                  15

Gly Leu Phe Gly Ala Ile Ala Gly Phe Ile Glu Gly Gly
                20                  25

<210> SEQ ID NO 17
<211> LENGTH: 34
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (34)..(34)
<223> OTHER INFORMATION: AMIDATION

<400> SEQUENCE: 17

Asp Gly Gln Glu Glu Lys Ala Gly Val Val Ser Thr Gly Leu Ile Gly
1               5                   10                  15

Gly Gly Leu Lys Ser Thr Gln Asn Ala Ile Asp Glu Ile Thr Asn Lys
                20                  25                  30

Val Asn

<210> SEQ ID NO 18
```

-continued

```
<211> LENGTH: 31
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (31)..(31)
<223> OTHER INFORMATION: AMIDATION

<400> SEQUENCE: 18

Asp Gly Gln Glu Glu Lys Ala Gly Val Val Ser Thr Gly Leu Ile Gly
1               5                   10                  15

Gly Gly Gly Leu Phe Gly Ala Ile Ala Gly Phe Ile Glu Gly Gly
            20                  25                  30

<210> SEQ ID NO 19
<211> LENGTH: 33
<212> TYPE: PRT
<213> ORGANISM: Artificial Sequence
<220> FEATURE:
<223> OTHER INFORMATION: synthesized peptide construct

<400> SEQUENCE: 19

Asp Gly Gln Glu Glu Lys Ala Gly Val Val Ser Thr Gly Leu Ile Gly
1               5                   10                  15

Gly Gly Asn Asp Ala Thr Tyr Gln Arg Thr Arg Ala Leu Val Arg Thr
            20                  25                  30

Gly

<210> SEQ ID NO 20
<211> LENGTH: 41
<212> TYPE: PRT
<213> ORGANISM: Artificial Sequence
<220> FEATURE:
<223> OTHER INFORMATION: synthesized peptide construct

<400> SEQUENCE: 20

Asp Gly Gln Glu Glu Lys Ala Gly Val Val Ser Thr Gly Leu Ile Gly
1               5                   10                  15

Gly Gly Ser Leu Leu Thr Glu Val Glu Thr Pro Ile Arg Asn Glu Trp
            20                  25                  30

Gly Cys Arg Cys Asn Asp Ser Ser Asp
        35                  40

<210> SEQ ID NO 21
<211> LENGTH: 32
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (16)..(16)
<223> OTHER INFORMATION: AMIDATION

<400> SEQUENCE: 21

Leu Lys Ser Thr Gln Asn Ala Ile Asp Glu Ile Thr Asn Lys Val Asn
1               5                   10                  15

Gly Gly Gly Asp Leu Leu Lys Asn Gly Glu Arg Ile Glu Lys Val Glu
            20                  25                  30

<210> SEQ ID NO 22
<211> LENGTH: 34
<212> TYPE: PRT
```

```
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (16)..(16)
<223> OTHER INFORMATION: AMIDATION

<400> SEQUENCE: 22

Leu Lys Ser Thr Gln Asn Ala Ile Asp Glu Ile Thr Asn Lys Val Asn
1               5                   10                  15

Gly Gly Gly Asp Gly Gln Glu Glu Lys Ala Gly Val Val Ser Thr Gly
            20                  25                  30

Leu Ile

<210> SEQ ID NO 23
<211> LENGTH: 28
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (13)..(13)
<223> OTHER INFORMATION: AMIDATION

<400> SEQUENCE: 23

Gly Leu Phe Gly Ala Ile Ala Gly Phe Ile Glu Gly Gly Gly Gly Asp
1               5                   10                  15

Leu Leu Lys Asn Gly Glu Arg Ile Glu Lys Val Glu
            20                  25

<210> SEQ ID NO 24
<211> LENGTH: 30
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (13)..(13)
<223> OTHER INFORMATION: AMIDATION

<400> SEQUENCE: 24

Gly Leu Phe Gly Ala Ile Ala Gly Phe Ile Glu Gly Gly Gly Gly Asp
1               5                   10                  15

Gly Gln Glu Glu Lys Ala Gly Val Val Ser Thr Gly Leu Ile
            20                  25                  30

<210> SEQ ID NO 25
<211> LENGTH: 39
<212> TYPE: PRT
<213> ORGANISM: Artificial Sequence
<220> FEATURE:
<223> OTHER INFORMATION: synthesized peptide construct

<400> SEQUENCE: 25

Ser Leu Leu Thr Glu Val Glu Thr Pro Ile Arg Asn Glu Trp Gly Ser
1               5                   10                  15

Arg Ser Asn Asp Ser Ser Asp Gly Gly Gly Asp Leu Leu Lys Asn Gly
            20                  25                  30

Glu Arg Ile Glu Lys Val Glu
        35

<210> SEQ ID NO 26
```

```
<211> LENGTH: 41
<212> TYPE: PRT
<213> ORGANISM: Artificial Sequence
<220> FEATURE:
<223> OTHER INFORMATION: synthesized peptide construct

<400> SEQUENCE: 26

Ser Leu Leu Thr Glu Val Glu Thr Pro Ile Arg Asn Glu Trp Gly Ser
1               5                   10                  15

Arg Ser Asn Asp Ser Ser Asp Gly Gly Gly Asp Gly Gln Glu Glu Lys
            20                  25                  30

Ala Gly Val Val Ser Thr Gly Leu Ile
        35                  40

<210> SEQ ID NO 27
<211> LENGTH: 30
<212> TYPE: PRT
<213> ORGANISM: Artificial Sequence
<220> FEATURE:
<223> OTHER INFORMATION: synthesized peptide construct

<400> SEQUENCE: 27

Asn Asp Ala Thr Tyr Gln Arg Thr Arg Leu Val Arg Thr Gly Gly Gly
1               5                   10                  15

Gly Asp Leu Leu Lys Asn Gly Glu Arg Ile Glu Lys Val Glu
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: synthesized peptide construct

<400> SEQUENCE: 28

Asn Asp Ala Thr Tyr Gln Arg Thr Arg Leu Val Arg Thr Gly Gly Gly
1               5                   10                  15

Gly Asp Gly Gln Glu Glu Lys Ala Gly Val Val Ser Thr Gly Leu Ile
            20                  25                  30

<210> SEQ ID NO 29
<211> LENGTH: 28
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (28)..(28)
<223> OTHER INFORMATION: AMIDATION

<400> SEQUENCE: 29

Asp Leu Leu Lys Asn Gly Glu Arg Ile Glu Lys Val Glu Gly Gly
1               5                   10                  15

Leu Phe Gly Ala Ile Ala Gly Phe Ile Glu Gly Gly
            20                  25

<210> SEQ ID NO 30
<211> LENGTH: 30
<212> TYPE: PRT
<213> ORGANISM: Artificial Sequence
<220> FEATURE:
<223> OTHER INFORMATION: synthesized peptide construct
<220> FEATURE:
<221> NAME/KEY: MOD_RES
<222> LOCATION: (30)..(30)
```

<223> OTHER INFORMATION: AMIDATION

<400> SEQUENCE: 30

Asp Gly Gln Glu Glu Lys Ala Gly Val Val Ser Thr Gly Leu Ile Gly
1               5                   10                  15

Gly Gly Leu Phe Gly Ala Ile Ala Gly Phe Ile Glu Gly Gly
            20                  25                  30

<210> SEQ ID NO 31
<211> LENGTH: 29
<212> TYPE: PRT
<213> ORGANISM: Artificial Sequence
<220> FEATURE:
<223> OTHER INFORMATION: synthesized peptide construct

<400> SEQUENCE: 31

Asn Asp Ala Thr Tyr Gln Arg Thr Arg Leu Val Arg Thr Gly Gly Gly
1               5                   10                  15

Asp Leu Leu Lys Asn Gly Glu Arg Ile Glu Lys Val Glu
            20                  25

<210> SEQ ID NO 32
<211> LENGTH: 31
<212> TYPE: PRT
<213> ORGANISM: Artificial Sequence
<220> FEATURE:
<223> OTHER INFORMATION: synthesized peptide construct

<400> SEQUENCE: 32

Asn Asp Ala Thr Tyr Gln Arg Thr Arg Leu Val Arg Thr Gly Gly Gly
1               5                   10                  15

Asp Gly Gln Glu Glu Lys Ala Gly Val Val Ser Thr Gly Leu Ile
            20                  25                  30

<210> SEQ ID NO 33
<211> LENGTH: 4
<212> TYPE: PRT
<213> ORGANISM: Artificial Sequence
<220> FEATURE:
<223> OTHER INFORMATION: Linker sequence

<400> SEQUENCE: 33

Gly Gly Gly Ser
1

<210> SEQ ID NO 34
<211> LENGTH: 36
<212> TYPE: PRT
<213> ORGANISM: Artificial Sequence
<220> FEATURE:
<223> OTHER INFORMATION: Heteroconjugate construct

<400> SEQUENCE: 34

Asp Leu Leu Lys Asn Gly Glu Arg Ile Glu Lys Val Glu Gly Gly Gly
1               5                   10                  15

Thr Gly Gly Lys Pro Gly Ile Ala Gly Phe Lys Gly Glu Gln Gly Pro
            20                  25                  30

Lys Gly Glu Pro
        35

<210> SEQ ID NO 35
<211> LENGTH: 30
<212> TYPE: PRT
<213> ORGANISM: Human immunodeficiency virus

```
<400> SEQUENCE: 35

Tyr Ser Val His Gln Arg Ile Asp Val Lys Asp Thr Lys Glu Ala Leu
1               5                   10                  15

Glu Lys Ile Glu Glu Glu Gln Asn Lys Ser Lys Lys Lys Ala
            20                  25                  30

<210> SEQ ID NO 36
<211> LENGTH: 46
<212> TYPE: PRT
<213> ORGANISM: Artificial Sequence
<220> FEATURE:
<223> OTHER INFORMATION: Heteroconjugate construct

<400> SEQUENCE: 36

Asp Leu Leu Lys Asn Gly Glu Arg Ile Glu Lys Val Glu Gly Gly Gly
1               5                   10                  15

Tyr Ser Val His Gln Arg Ile Asp Val Lys Asp Thr Lys Glu Ala Leu
            20                  25                  30

Glu Lys Ile Glu Glu Glu Gln Asn Lys Ser Lys Lys Lys Ala
        35                  40                  45
```

METHOD FOR INDUCING AN IMMUNE RESPONSE AGAINST AVIAN, SWINE, SPANISH, H1N1, H5N9 INFLUENZA VIRUSES AND FORMULATIONS THEREOF

CROSS-REFERENCE TO RELATED APPLICATIONS

This application is a national stage application of International Application Number PCT/US11/64746, filed on Dec. 13, 2011, claiming priority to U.S. Provisional Application No. 61/422,474, filed on Dec. 13, 2010.

REFERENCE TO SEQUENCE LISTING

This application contains a "Sequence Listing" submitted as an electronic .txt file named "SEQ_LST_ST25.txt." The subject matter of the "Sequence Listing" is incorporated herein by reference.

FIELD OF INVENTION

An innate system immunomodulator CEL-1000, DGQEEKAGVVSTGLI (SEQ ID NO. 6), or ICBL peptide J, DLLKNGERIEKVE (SEQ ID NO. 3), is used as an adjuvant alone and/or in conjunction with other adjuvants, such as water-in-oil (W/O) or oil-in-water (O/W) formulations, to induce an immune response in an animal subject infected with Type A influenza virus. The immunomodulator CEL-1000 or J can be applied in vaccine formulations and can be covalently linked to disease epitopes of viral diseases such as Type A Influenza viruses (H1N1, H5N1, H3N1, etc.), including "swine," "avian" or "bird," and "Spanish Influenza," as a method of treatment, prevention and/or as an adjuvant to be included with a flu vaccine. Varying dose regimens are further contemplated for Th1 immunomodulators such as CEL-1000 or J alone or as conjugates with viral epitopes used in initial priming with immunomodulating adjuvants and then boosting, with depot adjuvants and/or with immunogen only.

BACKGROUND

Each year, numerous individuals are infected with different strains and types of influenza virus. Infants, the elderly, those without adequate health care and immuno-compromised persons, and, in some cases, otherwise healthy adults who require protection from viral diseases without causing an immune response associated with a "cytokine-storm," are all at risk of death from such infections. Compounding the problem of influenza infections, novel influenza strains evolve readily and can spread amongst various species, thereby necessitating the continuous production of new vaccines. Although numerous vaccines capable of inducing a protective immune response specific for different influenza virus strains have been produced for over 50 years and include whole virus vaccines, split virus vaccines, surface antigen vaccines and live attenuated virus vaccines. New influenza vaccines are constantly required because of 1) mutations, 2) resortment of components between various strains, and 3) the continual emergence (or re-emergence) of different influenza strains.

Appropriate formulations of peptide heteroconjugates can stimulate and produce a systemic immune response. Peptide heteroconjugate technology has provided the ability to produce vaccines using genetic engineering (recombinant vaccines). Such vaccines are typically created using antigenic moieties of the newly emergent virus strains when polypeptides and polynucleotides of novel, newly emergent, or newly re-emergent virus strains are desired. The focus on most current vaccines is not on conserved proteins and, especially, essential regions of such conserved proteins or conserved regions of less conserved proteins, such as the neuramidinase (NA or N) or hemagglutin (HA or H) molecules found between various strains (e.g., H1N1, H1N5, H3N1, H1N9), but is more focused on the strain differences for these HA and NA molecules that account for the differences in H1 from H2, etc. or N1 from N2, etc.

One of these influenza epitopes is found in the 1918 "Spanish Influenza" pandemic. The 1918 Spanish influenza is similar to 2009 California H1N1 influenza, because there can be two initial mild waves late in a influenza season, and in 1918 and 1919 followed by a subsequent seasons with a severe, deadly disease with the propensity for affecting healthy immune systems with a cytokine storm (hypercytokinemia). However, the production of too many pro-inflammatory cytokines is thought to be a cause of death in the case of Type A influenza (e.g., H1N1), which is not addressed by current vaccines. A cytokine storm is caused by excessive amounts of pro-inflammatory cytokines and tends to occur in patients with stronger immune "robust" systems. There is a need for a formulation and a method of vaccination to combat a forthcoming deadly pandemic and to protect against new strains of type A influenza. These influenza viruses can be the most deadly for people in their prime, rather than affecting only the very young, the very old, or the most severely immunocompromised. There is also a need for an effective protective immune response without causing excessive amounts of pro-inflammatory cytokines that is effective against Type A influenza.

BRIEF SUMMARY

A vaccine for immunization of a mammal is provided against Type A influenza virus having an immunologically effective amount of peptide heteroconjugate DLLKNGERIEKVEGGGNDATYQRTRALVRTG (SEQ ID NO. 1) (J-NP), containing two elements of the LEAPS heteroconjugate construct namely a ICBL peptide J, DLLKNGERIEKVE (SEQ ID NO. 3) linked to a portion from the nucleoprotein (NP) of the A virus NDATYQRTRALVRTG (SEQ ID NO. 7) optionally in combination with an adjuvant. Another vaccine for immunization of a mammal against Type A influenza virus is provided having an immunologically effective amount of peptide heteroconjugate DLLKNGERIEKVEGGGSLLTEVETPIRNEWGCRCNDSSD (SEQ ID NO. 2), containing two elements of the LEAPS heteroconjugate construct namely a ICBL peptide J, DLLKNGERIEKVE (SEQ ID NO. 3) linked to a portion from the matrix 2 ectodomain (M2e) of the A virus SLLTEVETPIRNEWGCRCNDSSD (SEQ ID NO. 8) optionally in combination with an adjuvant. A vaccine for immunization of a mammal against Type A influenza virus is also provided having an immunologically effective amount of a mixture of peptide heteroconjugates SEQ ID. NO. 1 and SEQ ID NO. 2, optionally in combination with an adjuvant.

A therapeutic method of inducing an immune response in an animal subject infected with Type A influenza virus is provided by administering an immunologically effective amount of a mixture of the peptide heteroconjugate SEQ ID NO. 1, SEQ ID NO. 2, or others including the peptide J (SEQ ID NO. 3) or CEL-1000 conjugates with HA2 core 1, GLFGAIAGFIEGG (SEQ ID NO. 10) or HA2 core 2, LKSTQNAIDEITNKVN (SEQ ID NO. 9). A conjugate of Peptide J (SEQ ID NO. 3) and HA2 core 1, GLFGAIAGFIEGG (SEQ ID NO. 10), with a spacer GGG, is DLLKNGERIEKVEGGGGLFGAIAGFIEGG (SEQ ID NO. 16). A conjugate of Peptide J (SEQ ID NO. 3) and HA2 core 2, LKSTQNAIDEITNKVN (SEQ ID NO. 9), with a spacer GGG, is DLLKNGERIEKVEGGGLKSTQNAIDEITNKVN (SEQ ID NO. 15). Both HA2 core 1 (SEQ ID NO. 10) and HA2 core 2 (SEQ ID NO. 9) can be conjugated to the derG analogues of SEQ ID NOS. 7 and 8, optionally combined with an adjuvant.

A vaccine for immunization of a mammal against Type A influenza virus is provided having an immunologically effective amount of a mixture of peptide heteroconjugates SEQ ID. NO. 2 (J-M2e) combined with either SEQ ID NO. 15 (J-HA core 1) and SEQ ID NO. 16 (J-HA core 2), optionally in combination with an adjuvant. Further, a vaccine is contemplated containing any combination of sequences selected from the group consisting of SEQ ID NOS. 1-2 and 15-16, optionally in combination with an adjuvant.

A method for modulating a response to Type A influenza virus in a subject in need thereof is provided by combining precursors of dendritic cells from the subject with peptide heteroconjugate SEQ ID NO. 1, or another peptide heteroconjugate, ex vivo to form a mixture and administering the mixture to the subject. A method for modulating a response to Type A influenza virus in an infected subject is provided by differentiating precursors of dendritic cells from the subject ex vivo into more matured dendritic cells in the presence of a peptide heteroconjugate and introducing the more matured dendritic cells back into the subject. A method for modulating a response to Type A influenza virus in an infected subject is provided by treating isolated precursors of dendritic cells from blood derived monocytes and/or bone marrow taken from the subject with a peptide heteroconjugate to induce maturation of the precursors into more matured dendritic cells and administering, optionally without any supplementary immunomodulators, an effective amount of the L.E.A.P.S.-treated matured dendritic cells back into the subject. A method of inducing a systemic immune response to Type A influenza virus in an infected subject is provided by treating isolated precursors of dendritic cells from blood derived monocytes and/or bone marrow taken from the subject with a peptide heteroconjugate to induce maturation of the precursors into more matured dendritic cells, mixing the more matured dendritic cells with autologous T cells, and administering, optionally without any adjuvant, an effective amount of the mixture of cells to the subject.

One of ordinary skill in the art will appreciate that other aspects of this invention will become apparent upon reference to the following detailed description.

DETAILED DESCRIPTION

Figure 1:
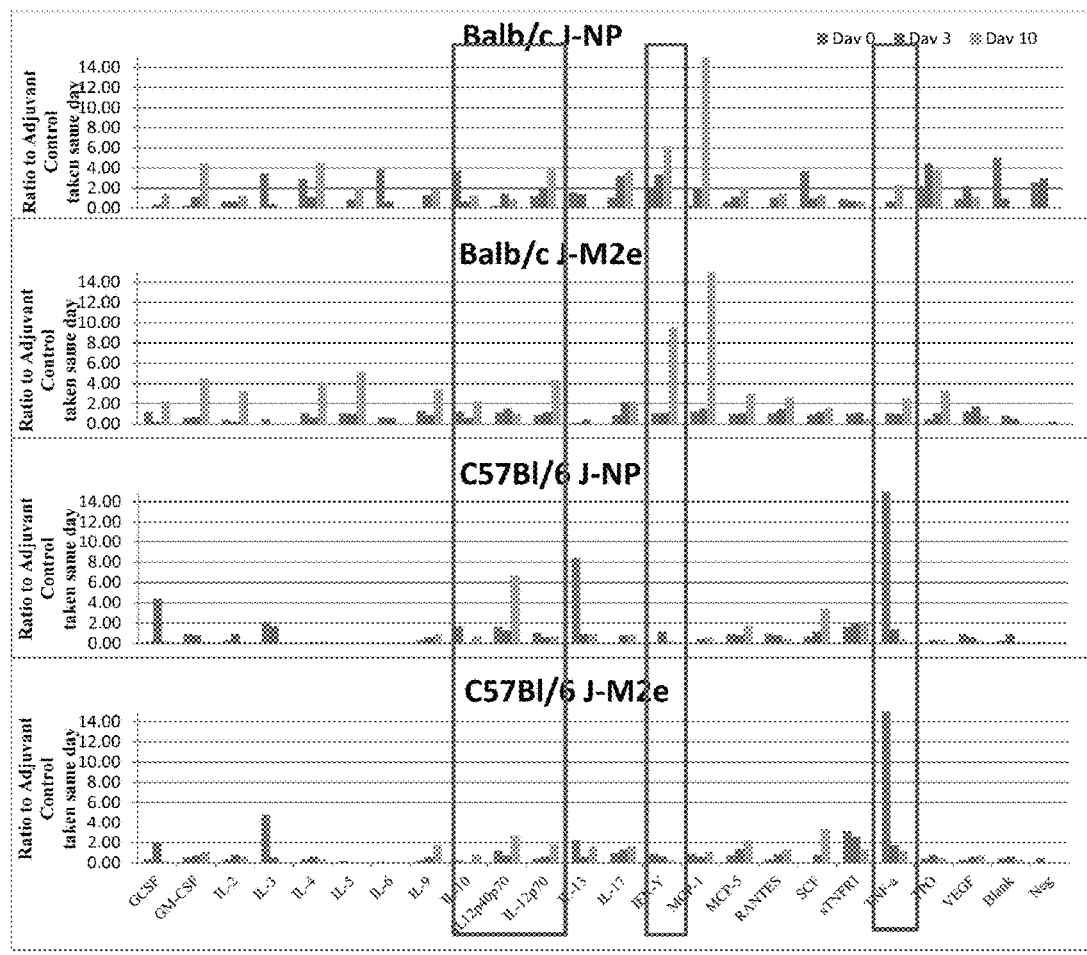
FIG. 1 shows the cytokine response of pooled sera for over 15 cytokines from sera taken at day 0, 3, and 10 for several groups of mice immunized with J-NP or J-M2e, each with an adjuvant plus an adjuvant control group and normalized to the adjuvant control for the same bleeding date and strain of mice.

The present invention provides peptide heteroconjugates useful for treatment of Type A influenza. The novel heteroconjugates bind in an antigen specific manner and redirect the T cell in the direction of a non-deleterious complete response. Alternatively, the novel heteroconjugates include one peptide component which will bind to T cells associated with Type A influenza while a second peptide component will bind to sites on the T cells which will preclude the normal sequence of events required for cell activation thereby initiating an abortative T cell modulation resulting in cell anergy and apoptosis.

Definitions

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "adjuvant" refers to substance that accelerates, prolongs or enhances antigen-specific immune responses when used in combination with vaccine antigens.

The terms "administering," "administer," "delivering," "deliver," "introducing," and "introduce" can be used interchangeably to indicate the introduction of a therapeutic or diagnostic agent into the body of a patient in need thereof to treat a disease or condition, and can further mean the introduction of any agent into the body for any purpose.

The term "antigen" refers to a substance or molecule that generates an immune response when introduced to the body or any molecule or fragment thereof now also refers to any molecule or molecular fragment that can be bound by a major histocompatibility complex (MHC).

The term "blood tissue" refers to cells suspended in or in contact with plasma.

The term "bone marrow cell" refers to any cell originating from the interior of bones.

The term "comprising" includes the recited steps, elements, structures or compositions of matter and does not exclude any un-recited elements, structures or compositions of matter.

The term "consisting of" includes and is limited to whatever follows the phrase the phrase "consisting of." Thus, the phrase indicates that the limited elements are required or mandatory and that no other elements may be present.

The phrase "consisting essentially of" includes any elements listed after the phrase and is limited to other elements that do not interfere with or contribute to the activity or action specified in the disclosure for the listed elements. Thus, the phrase indicates that the listed elements are required or mandatory but that other elements are optional and may or may not be present, depending upon whether or not they affect the activity or action of the listed elements.

A "dendritic cell" or "DC" refers to an antigen-presenting leukocyte that is found in the skin, mucosa, and lymphoid tissues and having a capability under appropriate conditions to initiate a primary immune response by activating T cells, lymphocytes and/or secreting cytokines.

The term "divalent linker" refers to any moiety having a structure forming a peptide bond to a first peptide moiety and forming a second bond to a second peptide moiety.

The term "effective amount" is an amount of a therapeutic which produces a therapeutic response, including an immune response, in the subject to which the therapeutic is administered.

The term "ex vivo" refers to an operation or procedure that is performed outside of the body of a patient or subject to be treated for an influenza viral disease. For example, an ex vivo procedure can be performed on living cells originating from the patient, subject or donor removed from the body. The term "autologous" refers to a situation where the donor and recipient of cells, fluids or other biological sample is the same person.

The terms "conjugate," "conjugation" and similar terms refer to two species being spatially associated with each other by covalent linkage, non-covalent binding or by a combination of covalent linkage and non-covalent binding. For example, an antibody can be conjugated to an epitope through non-covalent binding to the epitope as well as the antibody serving to conjugate the epitope (such as a cell surface marker) to a compound that is linked to the antibody.

An "immature dendritic cell" is a "dendritic cell" in a state characteristic of immune cells prior to contact with an antigen and having a limited present ability to active T cells, lymphocytes and/or to secrete cytokines; however, "immature dendritic cells" may acquire the ability to activate T cells, lymphocytes and secrete cytokines upon contact with an antigen.

The terms "immunomodulatory" and "immunoprotein" refer to a protein, peptide or cell having the ability to bind or interact with an immune cell to alter or to regulate one or more immune functions.

The term "infection" refers to the colonization in a host organism by a pathogenic influenza virus.

The term "Influenza virus" refers to an RNA virus from the Orthomyxoviridae family.

The term "Interleukin 12p70" refers to a cytokine produced by dendritic cells capable of directing the development of lymphocytes in a Th1 immune response.

The terms "isolated matured dendritic cells" or "isolated dendritic cells" refer to dendritic cells suspended in a liquid medium, a cell culture or a composition wherein at least 50% of the viable cells present in the liquid medium, the cell culture or the composition are dendritic cells or monocytes.

A "heteroconjugate" refers to a protein or peptide containing at least two amino acid sequences covalently linked to form a single molecule, wherein two sequences originate or are homologous to proteins expressed by different genes.

The term "maturation" refers to a process for generating a "matured dendritic cell."

The terms "matured dendritic cell," "maturated dendritic cell," "activated dendritic cell" or "effective dendritic cell" refer to a "dendritic cell" in a state characteristic of cells after contact with an antigen and having a present ability to initiate a primary immune response by activating T cells, lymphocytes and/or secreting cytokines.

The term "monocyte" refers to immune cells produced by bone marrow and haematopoietic stem cell having the ability to differentiate into macrophages or dendritic cells.

The terms "H1N1," "H5N1," "H7N3," "H9N2," and similar terms refer to specific subtypes of influenza Type A virus, where the numeral after "H" designates a type of hemagglutinin protein on the viral envelope and the numeral after "N" designates a type of neuraminidase as classified by the Centers for Disease Control and Prevention (Atlanta, Ga.).

The terms "originating" and "derived" as related to a peptide sequence refers to an organism or cell type that produces a protein containing the peptide sequence.

The terms "peptide" and "peptide construct" refer to a molecule including two or more amino acid residues linked by a peptide bond. The term "peptide" includes molecular species where only part of the molecule has peptide character and/or where two parts of the molecular species formed of peptide bonds are covalently linked by a divalent linker.

The term "red blood cells" refers to erythrocytes having an intact phospholipid bilayer membrane.

The term "subject" or "patient" refers to an animal, including mice and humans, to which a therapeutic agent is administered.

The term "systemic immune response" refers to an immune response where antibodies, cytokines or immune cells generated by the immune response are detectable throughout the circulatory and lymph systems of the body.

The term "T cell" refers to a lymphocyte having a T cell receptor protein on the surface of the cell.

"Type A influenza virus" refers to an RNA virus from the Orthomyxoviridae family characterized by the presence of at least three membrane proteins on the viral envelope: hemagglutinin, Neuraminidase and M2 proton-selective ion channel protein.

The terms "treating" and "treatment" as related to treating or treatment of immune cells refers to bringing an immune cell into contact with a substance or composition for a time period sufficient to cause a change in phenotype. The term "vaccine" refers to composition containing one or more antigens that stimulates an immune response when administered to an organism in vivo.

The term "virus" refers to a small infectious agent that can replicate only inside the living cells of another organism or host through the use of some of the host's own cellular machinery (e.g. ribosomes) for growth and replication. Viruses outside of the host cells are formed from a nucleic acid with an associated protein coat.

Immunomodulatory LEAPS™ Heteroconjugates

Specifically, the novel peptides of this invention include peptide heteroconjugates having the following formulae (I) or (II):

$$P_1\text{-}x\text{-}P_2 \quad (I)$$

$$P_2\text{-}x\text{-}P_1 \quad (II)$$

where $P_1$ is a peptide associated with Type A influenza and which will bind to an antigen receptor on a set or subset of T cells; $P_2$ is an immune response modifying peptide which will (i) cause a directed immune response by said set or subset of T cells or dendritic cells to which the peptide $P_1$ is attached and initiate an immune response focused on IL-12 without or with low levels of pro-inflammatory or inflammatory cytokines (Patricia R Taylor; Christopher A Paustian, Gary K Koski, Daniel H Zimmerman, K S Rosenthal, Maturation of dendritic cell precursors into IL12 producing DCs by J-LEAPS, *Cellular Immunology*, 2010; 262:1-5; Taylor P R, G K Koski, C C Paustian, P A Cohen, F B-G Moore, D H Zimmerman, K S Rosenthal, J-L.E.A.P.S.™ Vaccines Initiate Murine Th1 Responses By Activating Dendritic Cells, *Vaccine* 2010; 28:5533-4) or (ii) bind to a T cell receptor which will cause said set or subset of T cells to which the peptide $P_1$ is attached to initiate, but not complete, an immune response causing said set or subset of T cells to undergo anergy and apoptosis; and x is a direct bond or divalent linking group for covalently bonding $P_1$ and $P_2$.

Alternatively, the invention contemplates a variable immunomodulatory peptide heteroconjugate having the formula (III)

$$P_3\text{-}x\text{-}P_4 \quad (III)$$

where $P_3$ is a peptide heteroconjugate comprised of $X_1$ to $X_{14}$ said peptide $P_3$ being associated with Type A influenza essential highly conserved protein such as but not limited to the M2e or other matrix protein, NP1 nucleoprotein, and $P_4$ is a peptide heteroconjugate comprised of $X_1$ to $X_{14}$ causing a $T_h1$ directed immune response by said set or subset of T cells to which the peptide $P_3$ is attached or which binds to a dendritic cell or T cell receptor causing said set or subset of DC or T cells to which the peptide $P_3$ is attached to initiate and complete, an immune response.

Alternatively, the invention contemplates a variable immunomodulatory peptide heteroconjugate having the formula (IV)

$$P_5\text{-}x\text{-}P_6 \quad (IV)$$

where $P_5$ is a peptide heteroconjugate comprised of $X_1$ to $X_{14}$ said peptide $P_5$ being associated with Type A influenza, and $P_6$ is a peptide heteroconjugate comprised of $X_1$ to $X_{14}$ causing a $T_h2$ directed immune response by said set or subset of T cells to which the peptide $P_5$ is attached or which binds to a T cell receptor causing said set or subset of T cells to which the peptide $P_5$ is attached to initiate, but not complete, an immune response causing said set or subset of T cells to undergo anergy and apoptosis, such that $X_1$ to $X_{10}$ and $X_{14}$ describe a group of amino acids based on their features and $X_{11}$ to $X_{13}$ describe modifications to the peptide heteroconjugate, wherein $X_1$ is selected from the group consisting of Ala and Gly,
$X_2$ is selected from the group consisting of Asp and Glu,
$X_3$ is selected from the group consisting of Ile, Leu and Val,
$X_4$ is selected from the group consisting of Lys, Arg and His,
$X_5$ is selected from the group consisting of Cys and Ser,
$X_6$ is selected from the group consisting of Phe, Trp and Tyr,
$X_7$ is selected from the group consisting of Phe and Pro,
$X_8$ is selected from the group consisting of Met and Nle,
$X_9$ is selected from the group consisting of Asn and Gln,
$X_{10}$ is selected from the group consisting of Thr and Ser,
$X_{11}$ is $Gaba^x$ where $X_2X_3$, $X_3X_2$, $X_2X_3$, $X_3X_2$, $X_3X_3$, or $X_2X_2$ can be substituted with $X_{11}$;
$X_{12}$ is selected from the group consisting of acetyl, propionyl group, D glycine, D alanine and cyclohexylalanine;
$X_{13}$ is 5-aminopentanoic where any combination of 3 to 4 amino acids of $X_2$ and $X_3$ can be replaced with $X_{13}$;
$X_{14}$ is selected from the group consisting of $X_1$, $X_2$, $X_3$, $X_4$, $X_5$, $X_6$, $X_7$, $X_8$, $X_9$ and $X_{10}$; and
x is a direct bond or divalent linking group for covalently bonding $P_5$ and $P_6$.

In Formulae (I) and (II) and Formulae (III) and (IV), -x- represents a covalent bond or a divalent peptide linking group providing a covalent linkage between Peptide $P_1$ and Peptide $P_2$. In certain embodiments, -x- is a divalent peptide linking group having one or more glycine residues, such as the divalent linking group -GGG-, -GG- or -GGGS- (SEQ ID NO. 33). In order to avoid synthesis and or purifications of peptides having four glycine residues in a row, which may be difficult to synthesize and purify, a linking group of only 2G i.e. -GG- can be used. In certain embodiments, peptide $P_1$ is selected from SEQ ID NO.'s 7-10 or variants thereof. In certain embodiments, peptide $P_2$ is selected from SEQ ID NO.'s 3 and 6 or variants thereof.

In certain embodiments, the divalent linking group is not limited to any particular identity so long as the linking group -x- serves to covalently attach the Peptide$_{P1}$ and Peptide$_{P2}$ as shown in Formulae (I) and (II). The linking group -x- can contain one or more amino acid residues or a bifunctional chemical linking group, such as, for example, N-succinimidyl-3-(2-pyridyldithio)propionate (SPDP), m-maleimidobenzoyl-N-hydroxy-succimide ester (MBS), or 1-ethyl-3-(3-dimethylaminopropyl)carbodiimide (EDC). In certain embodiments, the linking group -x- can be a direct peptide or other covalent bond directly coupling Peptide$_{P1}$ and Peptide$_{P2}$. In certain embodiments where the linking group -x- contains amino acid residues, the linking group -x- can contain from 1 to about 5 amino acid residues or from 1 to about 3 amino residues. In certain embodiments, the linking group -x- can be cleavable or non-cleavable under physiological conditions.

The peptide heteroconjugates of Formulae (I) and (II), or Formulae (III) and (IV), can be modified including modifications to the N- or C-terminal of the heteroconjugates. The peptide heteroconjugates can contain a sequence of amino acid residues consistent with the described Peptide $P_1$ and Peptide $P_2$. However, the N- or C-terminal of the described peptide conjugates can be modified by any one or more of amidation or acylation, including myristoylation. A peptide having such N- or C-terminal modification can be referred to as a variant to any of the peptides described herein.

In certain embodiments, variants of Peptides $P_1$ and $P_2$ as well as variants of any of the described peptide heteroconjugates includes sequence variants. Such variant are herein defined as a sequence wherein 1, 2, 3, 4 or 5 amino acid residues of any of SEQ ID No.'s 1-32 or any other sequence disclosed herein are replaced with a different amino acid residue without affecting the ability of a peptide conjugate to stimulate an immune response. In certain embodiments, variants to SEQ ID No.'s 1-32 have amino acid residues substituted in a conserved manner. In certain other embodiments, variants to SEQ ID No.'s 1-32 or any other sequence disclosed herein have amino acid residues substituted in a non-conserved manner. Variants to SEQ ID No.'s 1-32 or any other sequence disclosed herein include amino acid sequences where 1, 2, 3, 4 or 5 amino acid residues are deleted from the sequences and/or 1, 2, 3, 4 or 5 amino acid residues are added to the sequences. Variants include embodiments where combinations of conserved or non-conserved substitutions, additions and/or deletions are made to a sequence where a total of 1, 2, 3, 4 or 5 such substitutions are made.

A conserved substitution is a substitution where an amino acid residue is replaced with another amino acid residue having similar charge, polarity, hydrophobicity, chemical functionality, size and/or shape. Substitution of an amino acid residue in any of the following groups with an amino acid residue from the same group is considered to be a conserved substitution: 1) Ala and Gly; 2) Asp and Glu; 3) Ile, Leu, Val and Ala; 4) Lys, Arg and His; 5) Cys and Ser; 6) Phe, Trp and Tyr; 7) Phe and Pro; 8) Met and Nle (norleucine); 9) Asn and Gln; and 10) Thr and Ser.

A vaccine made up of SEQ ID NO. 1 and SEQ ID NO. 2, individually, or a mixture thereof, can allow the targeting of "mutated" versions of H1N1 swine and other influenza viruses. The vaccines focus on the conserved, non changing epitopes of the different strains of Type A Influenza viruses (H1N1, H5N1, H3N1, etc.), including "swine," "avian" or "bird," and "Spanish Influenza," in order to minimize the chance of viral "escape by mutations" from immune recognition. The vaccines contain epitopes known to be associated with immune protection against influenza in animal models. The use of L.E.A.P.S. vaccine technology for immunization in animal models has been shown to provide protection from viral diseases without causing an immune response associated with the deadly "cytokine-storm" seen in many of the victims of influenza. The present invention also provides new and/or newly isolated influenza hemagglutinin and neuraminidase variants that are capable of use in production of numerous types of vaccines as well as in research, diagnostics, etc. Numerous other benefits will become apparent upon review of the following.

The T cell binding ligands associated with TH2 responses are for example, peptide G from MHC class II (Zimmerman et al., A new approach to T cell activation: natural and synthetic conjugates capable of activating T cells, Vacc. Res., 1996; 5:91, 5:102; Rosenthal et al., Immunization with a LEAPS™ heteroconjugate containing a CTL epitope and a peptide from beta-2-microglobulin elicits a protective and DTH response to herpes simplex virus type 1, Vaccine, 1999; 17(6):535-542), IL-4 or IL-5 or peptides known to stimulate IL-4 or IL-5 synthesis are used as the ICBL (immune cell binding ligand) along with the autoimmune inducing peptide (e.g., Hammer et al., HLA class I peptide binding specificity and autoimmunity, Adv. Immunol., 1997; 66:67; Ruiz et al., Suppressive Immunization with DNA Encoding a Self-Peptide Prevents Autoimmune Disease: Modulation of T Cell Costimulation, J. Immunol., 1999; 162:3336; Krco et al., Identification of T Cell Determinants on Human Type II Collagen Recognized by HLA-DQ8 and HLA-DQ6Transgenic Mice, J. Immunol., 1999; 163:1661; Araga et al., A Complementary Peptide Vaccine That Induces T Cell Anergy and Prevents Experimental Allergic Neuritis in Lewis Rats, J. Immunol., 1999; 163:476-482; Ota et al., T-cell recognition of an immunodominant myelin basic protein epitope in multiple sclerosis, Nature, 1990; 346:183; Yoon et al., Control of Autoimmune Diabetes in NOD Mice by GAD Expression or Suppression in β Cells, Science, 1999; 284:1183; Dittel et al., Presentation of the Self Antigen Myelin Basic Protein by Dendritic Cells Leads to Experimental Autoimmune Encephalomyelitis, J. Immunol., 1999; 163:32; Gautam et al., A Viral Peptide with Limited Homology to a Self Peptide Can Induce Clinical Signs of Experimental Autoimmune Encephalomyelitis, J. Immunol., 1998; 161:60, the disclosures of which are incorporated herein by reference thereto) in the peptide conjugate. In an animal model the mechanism of diabetes prevention in the RIP-NP model was shown to be mediated by insulin β-chain, and IL-4 producing regulatory cells acting as bystander suppressors (Homann et al., Insulin in Oral Immune "Tolerance": A One-Amino Acid Change in the B Chain Makes the Difference, J. Immunol., 1999; 163:1833).

An ICBL involved in CD28 costimulation (Kubo et al., CD28 Costimulation Accelerates IL-4 Receptor Sensitivity and IL-4-Mediated Th2 Differentiation, J. Immunol., 1999; 163:2432) could also be effective for this purpose. The ICBL such as peptide J, DLLKNGERIEKVE (SEQ ID NO. 3) (Zimmerman et al., supra; Rosenthal et al., supra) or ones known to stimulate IL-2 or IL-12 synthesis can be used. For example, with a linker "GGG" is shown by SEQ ID NO. 4.

DLLKNGERIEKVEGGG (SEQ ID NO. 4)

The improved variants of above peptide are shown as follows:

$X_2X_3X_3X_4X_9X_1X_2X_4X_3X_2X_4X_3X_2$ or
$X_{12}X_2X_3X_3X_4X_9X_1X_2X_4X_3X_2X_4X_3X_2$ or
$X_{12}X_{11}X_4X_9X_1X_2X_4X_{11}X_4X_{11}$ or
$X_{12}X_{13}X_4X_9X_1X_2X_4X_{11}X_4X_{11}$ or

Optionally, CEL-1000 can be used as the ICBL, which is an 18 amino acid peptide having a molecular weight of ~1.7 Kda and variants thereof derived from the second domain of the β-chain of human MHC-II being a modified version of a human immune-based protein known to bind both human and mouse immune cells. The 18 amino acid peptide corresponds to aa135-149 of the β-chain of MHC II and the human counterpart (MHC II $β_{134-148}$) binds to murine as well as human CD4+ cells. The chemical structure of CEL-1000 using the one-letter amino acid abbreviations, free amino and amidated carboxyl termini with the molecular formula is: (amino)-DGQEEKAGVVSTGLIGGG-(amide) (SEQ ID NO. 5), (amino)-DGQEEKAGVVSTGLI-(amide) (SEQ ID NO. 6) without a GGG linker sequence. CEL-1000 is prepared by F-MOC chemistry and purified by Reverse Phase (RP)-HPLC, analyzed by another RP-PLC system, ion exchange chromatography (IEC)-HPLC as well as mass spectroscopy.

Based on site directed mutagenesis studies of MHC II β-chain and/or peptide competition studies, peptides such as CEL-1000, were shown to bind to CD4, a T cell co-stimulator molecule (Charoenvit et al., A small peptide derived from human MHC β2 chain induces complete protection against malaria in an antigen-independent manner, Antimicrobial Agents and Chemotherapy, July 2004; 48(7):2455-63; Cammarota et al., Identification of a CD4 binding site on the beta 2 domain of HLA-DR molecules, Nature, 1992; 356:799-801) and cell surface protein on some Dendritic Cell (DCs) (Konig, et al., MHC class II interaction with CD4 medicated by a region analogous to the MHC class I binding site for CD8, Nature, 1992; 356:796-798; Shen X. and Konig R., "Regulation of T cell immunity and tolerance in vivo by CD4", Int. Immunol., 1998 10:247-57; Shen X. et al., Peptides corresponding to CD4-interacting regions of murine MHC class II molecules modulate immune responses of CD4+ T lymphocytes in vitro and in vivo, J Immunol., 1996; 157:87-100).

Studies of a murine homologous sequence from I-A $β^k$ showed induced stimulation of Ag-specific Th1 immune responses and inhibition of activation induced cell death (AICD) following multiple administrations at high doses. Also from Konig's group, it is known that following Ag specific in vitro stimulation (IVS), enhanced IFN-γ levels are observed.

Induction of an optimal immune response to a vaccine requires mimicking nature's approach to immunization. Dendritic Cells (DCs) also play a major role in initiating and directing the immune response to a vaccine. The initial host response to an antigen (Ag) requires internalization of the Ag into the DC, processing and presentation by the MHC I or II for T cell recognition. DCs, macrophages and B cells are capable of presenting Ags to CD4+ helper T cells and CD8+ cytotoxic T cells as peptides held within grooves of the class II and I MHC proteins, respectively. Myeloid DCs are most likely to be involved in antigen presentation. After taking up antigen and with appropriate stimulation, DCs migrate to the T-cell rich areas of lymphoid tissues, where they stimulate Ag-specific T cells. These cells can be functionally divided into DC1 and DC2 cell types based on the means of their activation, their cytokine output and the nature of their influence on T cells. DC1 cells produce IL12 and promote Th1 type responses whereas DC2 cells promote Th2 type responses.

Development of DC1 or DC2 cells is determined by environmental factors, including dose and form of the Ag, but mostly by stimulation of Toll Like Receptors (TLR) and other receptors for microbial pathogen associated molecular patterns, artificial ligands of these receptors and other stimuli. Many of these TLR molecules are triggered by adjuvants made from the TLR ligands such as Lipid A, MPL, CpG, LPS, etc. Other receptors on DC known as LIR (leukocyte immunoglobulin like receptors or also known as CD85) are known to recognize self epitopes found on various MHC molecules. Both CEL-1000 and peptide J are derived from MCH molecules and are likely ligands for these LIR. Many of these receptors' responses are also triggered by their own adjuvants. (Annunziato F. et al., Expression and release of LAG-3-encoded protein by human CD4+ T cells are associated with IFN-gamma production, FASEB J., 1996 May; 10(7):769-76; Anderson K J, Allen R L., Regulation of T-cell immunity by leucocyte immunoglobulin-like receptors: innate immune receptors for self on antigen-presenting cells, Immunology, 2009 May; 127(1): 8-17; Sloane D E et al., Leukocyte immunoglobulin-like receptors: novel innate receptors for human basophil activation and inhibition, Blood, 2004 Nov. 1; 104(9):2832-9; Shiroishi M et al., Efficient leukocyte Ig-like receptor signaling and crystal structure of disulfide-linked HLA-G dimer, J. Biol. Chem., 2006 Apr. 14; 281(15):10439-47; Shiroishi M et al., Human inhibitory receptors Ig-like transcript 2 (ILT2) and ILT4 compete with CD8 for MHC class I binding and bind preferentially to HLA-G, Proc. Natl. Acad. Sci. USA. 2003 Jul. 22; 100(15):8856-61; Colonna M et al., A novel family of Ig-like receptors for HLA class I molecules that modulate function of lymphoid and myeloid cells, J. Leukoc. Biol., 1999 September; 66(3):3; 75-81; Borges L, et al., A family of human lymphoid and myeloid Ig-like receptors, some of which bind to MHC class I molecules, J Immunol., 1997 Dec. 1; 159(11):5192-6; Shiroishi M et al., Structural basis for recognition of the nonclassical MHC molecule HLA-G by the leukocyte Ig-like receptor B2 (LILRB2/LIR2/ILT4/CD85d), Proc. Natl. Acad. Sci. U.S.A., 2006 Oct. 31; 103(44):16412-7).

These peptide-based vaccines can provide prophylactic protection and also have the potential for therapeutic treatment of recurrent disease. The L.E.A.P.S. technology is a T-cell modulation platform technology that can be used to design and synthesize proprietary immunogens for any disease for which an antigenic sequence has been identified, such as infectious, parasitic, malignant, or autoimmune diseases and allergies.

Each L.E.A.P.S. heteroconjugate is composed of an Immune/T cell binding ligand (ICBL) which has the ability to induce and elicit protective immunity and antigen specific response in animal models.

L.E.A.P.S. technology directly mimics cell to cell interactions on the dendritic and T-cell surface using synthetic peptides. The L.E.A.P.S. heteroconjugates containing the antigenic disease epitope linked to an Immune/T-cell binding ligand (ICBL) can be manufactured by peptide synthesis or by covalently linking two peptides. Depending on the type of L.E.A.P.S. heteroconjugates and ICBL used, the peptide heteroconjugate is able to direct the outcome of the immune response towards the development of T-cell function with primary effector T-cell functions: T Lymphocyte; helper/effector T Lymphocyte, type 1 or 2 (Th1 or Th2), cytotoxic (Tc) or suppressor (Ts) without excessive amounts of proinflammatory and inflammatory cytokines.

The type of the immune response elicited against an immunogen or a natural infection can be classified as TH1/Tc1, Th2/Tc2 or Th3 based on the predominant IgG subtype, the cytokines that are induced, or the presence or absence of delayed type hypersensitivity (DTH) response. A TH0 response is an earlier response that can mature into either a TH1 or a TH2 response and has features of both. The TH1 (CD4)/Tc1 (CD8) response is characterized by activation of $CD4^+$ and $CD8^+$ T cells to produce IL-2, TNF-β, and IFN-γ and to promote the production of IgM and specific IgG antibody subtypes and cell-mediated immune responses including delayed-type hypersensitivity (DTH). These responses reinforce early, local and inflammatory responses. Th2 responses promote different IgG subclasses, IgE and IgA responses but not cell mediated responses to antigen (Ag). Th2 responses prevent the onset of protective Th1 cell mediated responses important for infection control, which may exacerbate disease. Initiation of Th1 and Th2 T cells has important implications in terms of resistance and susceptibility to disease. Th1-dominated responses are potentially effective in eradicating infectious agents, especially viruses and intracellular infections, and are important for the induction of cytotoxic T lymphocytes (CTL). In contrast, Th2 T cell responses are insufficient to protect against challenge with intracellular infections but can provide protection against parasites and extracellular agents that can be neutralized by antibodies and against autoimmunity. Most importantly, for many vaccines it is thought that initiation of immunity with a Th1 response and then progression to a Th2 response promotes better immune memory.

The L.E.A.P.S. heteroconjugate ICBLs are coupled to different and known highly conserved peptide protective epitopes from different essential proteins common to all influenza A virus strains, including avian and swine influenza, and identified in the current strains spreading around the world. One epitope is a known protective T and B cell epitope, and the other is a known B cell epitope that might also contain a T epitope.

The epitopes chosen are known to reduce morbidity and mortality in single epitope vaccines using specific peptide carrier elements in animal models. The highly variable hemagglutin (HA or H) and neuramidase (NA or N) proteins found in most vaccines are eliminated. These proteins are associated with sterilizing immunity. However, most epitopes are from these proteins also very strain-specific, and their immuno-dominant nature is thought to be the reason that a new, modified influenza vaccine formulation is required each year, having recognition for these variable epitopes. The production of influenza virus vaccines using L.E.A.P.S. technology minimizes the influence of genetic heterogeneity of man as well as the large genetic drift seen in influenza A virus strains. There are some regions of the HA and NA molecules that contain conserved regions associated with viral functions and efforts will be to use those regions and avoid use of strain specific epitopes.

By using these conserved epitopes, the focus is on epitopes found in all strains of type A influenza, e.g., H1N1, H5N9, and H3N1, including avian and swine flu. The strains are not limited to any one of these strains that have been reported in the last few years and are currently the focus of vaccine manufacturers, but also include strains that have changed from year to year from 2004-2009 as well as that which is known as Spanish influenza. These epitopes are selected from ones known to be associated with immune protection in animal influenza models. By formulating several L.E.A.P.S. heteroconjugates, there is a reduced probability that several rare mutations will occur that alter the function of these conserved essential proteins. Use of the highly variable strain-specific H and N antigens found in most currently licensed vaccines is avoided. This is important, because while antibodies to H and N antigens are used as surrogate markers for protection, immune responses to most of the epitopes of these two proteins H (or HA) and N may contribute to a cytokine storm. Additionally, by using only selected important and essential epitopes of the H and N proteins, it is not necessary to use epitopes that may normally contribute to the generation of immunodominant responses, some of which may be protective and others of which are not protective as stated, but rather, may be involved in the generation of acute phase proinflammatory cytokines such as TNF-α, IL-1, and IL-6 seen in the cytokine storm. As an additional benefit, the present invention facilitates innate immune protection until post-vaccination adaptive immunity is established. This use would be especially beneficial for individuals who are at high risk because the invention is an immunomodulator that acts on the innate immune system.

Recently, several critically important epitopes of the HA2 subunit protein of the hemagglutinin molecule have been identified which have a critical and essential role in the natural life cycle of the virus and also which monoclonal antibodies are directed against to block the infectious process. (Prabhu N. et al., Monoclonal antibodies against the fusion peptide of hemagglutinin protect mice from lethal influenza A virus H5N1 infection, J. Virol., March 2009; 83(6):2553-62, epub Dec. 24, 2008; Sui J. et al., Structural and functional bases for broad-spectrum neutralization of avian and human influenza A viruses, Nat. Struct. Mol. Biol., March 2009; 16(3):233-4. Ekiert D. C. et al., Antibody recognition of a highly conserved influenza virus epitope, Science, Apr. 10, 2009; 324(5924):246-51, epub Feb. 26, 2009). Using the above information and examining the sequence around these points and considerations in manufacturing such as avoidance of NG regions, 2 epitopes were selected from the beginning of HA2, the so called fusion peptide region HA2 core 1, GLFGAIAGFIEGG (SEQ ID NO. 10) and, further down the HA2 molecule, a site intimately involved in the infection process HA2 core 2, LKSTQNAIDEITNKVN (SEQ ID NO. 9) to make into L.E.A.P.S. heteroconjugates with the previously mentioned ICBL peptide J DLLKNGERIEKVE (SEQ ID NO. 3) and CEL-1000 DGQEEKAGVVSTGLI (SEQ ID NO. 4) as follows: DLLKNGERIEKVEGGGLKSTQNAIDEITNKVN (SEQ ID NO. 15), DGQEEKAGVVSTGLIGGGLKSTQNAIDEITNKVN (SEQ ID NO. 17), DLLKNGERIEKVEGGGGLFGAIAGFIEGG (SEQ ID NO. 16) and DGQEEKAGVVSTGLIGGGGLFGAIAGFIEGG (SEQ ID NO. 18). It is known to those of ordinary skill in the art that synthesizing four consecutive Gs can be difficult. Hence, in some embodiments, a G for these conjugates containing the HA2 core 1 peptide GLFGAIAGFIEGG (SEQ ID NO. 10) can be deleted from the 5' end prior to conjugation, as shown by the following sequences: DLLKNGERIEKVEGGGLFGAIAGFIEGG (SEQ ID NO. 29) and DGQEEKAGVVSTGLIGGGLFGAIAGFIEGG (SEQ ID NO. 30).

At the same time, heteroconjugates of derG (CEL-1000) DGQEEKAGVVSTGLIGGG-(amide) (SEQ ID NO. 5) of both the NP and M2e epitopes, respectfully, were designed as L.E.A.P.S. conjugates DGQEEKAGVVSTGLIGGGN-DATYQRTRALVRTG (SEQ ID NO. 19) DGQEEKAGVVSTGLIGGGSLLTEVETPIRNEWGCRCNDSSD (SEQ ID NO. 20) for further use. Table 1 shows the L.E.A.P.S. conjugates, including permutations of heteroconjugates of derG (CEL-1000) and peptide J of the NP and M2e epitopes or the HA2 core 1 and HA2 core 2 peptides.

TABLE 1

| Conjugates | SEQ ID NO. |
|---|---|
| DLLKNGERIEKVEGGGNDATYQRTRLVRTG | 1 |
| DLLKNGERIEKVEGGGSLLTEVETPIRNEWGSRSNDSSD | 2 |
| DLLKNGERIEKVEGGGLKSTQNAIDEITNKVN | 15 |
| DLLKNGERIEKVEGGGGLFGAIAGFIEGG | 16 |
| DGQEEKAGVVSTGLIGGGLKSTQNAIDEITNKVN | 17 |
| DGQEEKAGVVSTGLIGGGGLFGAIAGFIEGG | 18 |
| DGQEEKAGVVSTGLIGGGNDATYQRTRALVRTG | 19 |
| DGQEEKAGVVSTGLIGGGSLLTEVETPIRNEWGCRCNDSSD | 20 |
| LKSTQNAIDEITNKVNGGGDLLKNGERIEKV | 21 |
| LKSTQNAIDEITNKVNGGGDGQEEKAGVVSTGLI | 22 |
| GLFGAIAGFIEGGGGDLLKNGERIEKVE | 23 |
| GLFGAIAGFIEGGGGDGQEEKAGVVSTGLI | 24 |
| SLLTEVETPIRNEWGSRSNDSSDGGGDLLKNGERIEKV | 25 |
| SLLTEVETPIRNEWGSRSNDSSDGGGDGQEEKAGVVSTGLI | 26 |
| NDATYQRTRLVRTGGGGDLLKNGERIEKVE | 27 |
| NDATYQRTRLVRTGGGGDGQEEKAGVVSTGLI | 28 |
| DLLKNGERIEKVEGGGLFGAIAGFIEGG | 29 |
| DGQEEKAGVVSTGLIGGGLFGAIAGFIEGG | 30 |
| NDATYQRTRLVRTGGGDLLKNGERIEKVE | 31 |
| NDATYQRTRLVRTGGGDGQEEKAGVVSTGLI | 32 |

Vaccines normally take several months to evoke a response. The evaluation of the initial in vivo phase of vaccine is followed by assays for panels of cytokines and antibodies, as applicable. The results will determine if a booster, which is normally needed, is necessary. More animal studies follow, including a challenge or surrogate model and studies using human DCs.

A preparation and formulation of CEL-1000 is provided that can easily be prepared as a GMP formulated product and used in GLP or GCP conditions for toxicology and clinical studies respectfully. A sterile pyrogen free proprietary formulation of 2 mg/mL of CEL-1000 in PBS and trehalose, lyophilized and reconstituted prior to use with unopened water for injection (WFI) is contemplated. This formulation has shown to be extremely stable for over 2 years at 2-8° C. CEL-1000 was evaluated as a co-adjuvant with several different recombinant protein antigens.

The co-adjuvants include products such as GMP products including ISA-51 (Seppic, currently in phase III studies), Depovax, a patented liposomal adjuvant currently in phase I trials by Immunovaccine Technologies, and MAS1, a proprietary water-in-oil GMP adjuvant from MerciaPharma currently in phase II clinical studies. Alum is currently the only FDA licensed adjuvant of the group. The MAS1 (PMA-0003) that were used were a non GMP grade.

Freund's adjuvants, complete and incomplete, are also contemplated (Sigma Corp., St. Louis, Mo.). For Product Number F5881 and F5506, the Storage Temperature is 2-8° C. where F5881 is a clear amber liquid containing particulate matter (dried cells). F5506 is a clear amber liquid. Freund's Adjuvant is one of the most commonly used adjuvants in research. It is used as a water-in-oil emulsion. It is prepared from non-metabolizable oils (paraffin oil and mannide monooleate). If it also contains killed *Mycobacterium tuberculosis*, then it is known as Complete Freund's Adjuvant. Without the bacteria, it is Incomplete Freund's Adjuvant. First developed by Jules Freund in the 1940's, Freund's Adjuvant is designed to provide continuous release of antigens necessary for stimulating a strong, persistent immune response. The main disadvantage of Freund's Adjuvant is that it can cause granulomas, inflammation at the inoculation site and lesions. The mycobacteria subcellular components in Complete Freund's attract macrophages and other cells to the injection site, which enhances the immune response. For this reason, the Complete Freund's Adjuvant is used only for the initial injections. To minimize side-effects, Incomplete Freund's Adjuvant is used for the boosts. (Freund, J. and McDermott, K., Proc. Soc. Exp. Biol. Med., 1942; 49:548-553; Freund, J., Ann. Rev. Microbiol., 1947; 1:291; Freund, J., Adv. Tuberc. Res., 1956; 7:130; Bennett, B. et al., J. Immuno. Meth., 1992; 153:31-40; Deeb, B. J. et al., J. Immuno. Meth., 1992; 152:105-113; Harlow, E. and Lane, D., Antibodies: A Laboratory Manual, Cold Spring Harbor Laboratory, 1988).

Freund determined that a second boost of Complete Freund's Adjuvant was actually detrimental and caused deaths presumably due to the reactogenic nature of the killed *Mycobacterium*. Several of the molecules in Complete Freund's Adjuvant are known potent stimulators of TLR and other receptors for the innate response.

As an illustration of another type of a conjugate for application in Rheumatoid Arthritis, CEL-2000 (DLLKNGERIEKVEGGGTGGKPGIAGFKGEQGPK-GEP, SEQ ID NO. 34) as described in U.S. Pat. Publication 2011/0098444 A1, the contents of which are incorporated herein by reference, composed of the peptide J and a collagen peptide, is being used as a vaccine for rheumatoid arthritis and has been demonstrated to be safe and well-tolerated in mice receiving five (5) doses of vaccine therapy and to suppress disease over a 90 day period. Having demonstrated efficacy in the mouse, further development for human use is anticipated through demonstration that these vaccines act and stimulate human Dendritic Cells (DCs) in a similar manner as with isolated murine DCs. Data supports L.E.A.P.S. conjugates acting at interface of innate and adaptive immunity. There is no evidence for cytokine storm (hypercytokinemia) being generated from either in vivo or in vitro use to date with three different L.E.A.P.S. conjugates evaluated. (Zimmerman D H, P Taylor, A Bendele, R Carambula, Y Duzant, S P O'Neill, E Talor, K S Rosenthal, CEL-2000: A Therapeutic Vaccine for Rheumatoid Arthritis Arrests Disease Development and Alters Serum Cytokine/Chemokine Patterns in the Bovine Collagen Type II Induced arthritis in the DBA Mouse Model, Int. Immunopharmacol., 2010; 10:412-421; see also Cihakova D, J G Barin, M Kimura, G C Baldeviano, M V Talor, D H Zimmerman, E Talor, N R Rose, Conjugated Peptide Ligand is Able to Prevent and Treat Experimental Autoimmune Myocarditis, is a Strong Stimulator of Cell and Humoral Immunity, Int. Immunopharmacol., 2008; 8:624-633).

CEL-2000 is more effective than Enbrel, in CIA model of RA by AI score, footpad swelling histopathological results. CEL-2000 therapy results in important serum cytokine changes, as expected, including increased IL-12p70 and IL-10 and reduced TNF-α, IL-1, MCP-1, among others, and possibly including IL-23 based on a decrease in IL-12p40. CEL-2000 is safe and well-tolerated over 90 days with 5 injections of 100 nMoles in adjuvant 14 days apart. CEL-2000 has been shown in limited studies to act on murine DCs and human DCs as the L.E.A.P.S. conjugates, but with an altered IL-10 pattern.

Studies of other L.E.A.P.S. vaccines also show in vivo protection by L.E.A.P.S. heteroconjugates in various challenge models. There are antigen-specific delayed type hypersensitivity responses. Monoclonal antibody ablation using in vivo animal HSV-1 challenge protection model and DTH for HIV immunogen immunization identify the cells and cytokines involved. Serum antibody evaluation in several non-challenge mouse and rabbit models and EAM and HSV-1 challenge models show the expected isotope for protective responses in challenge models. Serum cytokine modulation provides a decrease in IL-10 and an increase in IL-12 and IFN-γ by days 3 to 10. There was ex vivo induction and expression of cytokines using different L.E.A.P.S. conjugates HSV and HIV that are similar to CEL-1000 in size and composition, other than the antigenic component, of immature DC differentiation and maturation into mature DCs with morphological changes including dendritic projections, typical DC CD86 and other markers expression and cytokine IL-12 production with cells from various organs such as murine bone marrow and human blood.

EXAMPLE 1

An immunogenicity study of H1N1 or swine flu L.E.A.P.S. conjugate in BALB/c and C57BL6 mice is, for example, as follows:

The in vivo phase of the animal studies were done by Washington Biotech Incorporated and approved by their Institution's Animal Use Committee, and the experiments outlined herein were conducted according to the principles set forth in the "Guide for the Care and Use of Laboratory Animals." All pools were made at time of thaw of sera at Cel-Sci (Vienna, Va.).

Studies of four to six groups of eight BALB/c per group and later C57BL6 mice were injected with adjuvant and antigen in PBS (ISA51) in 0.10 mL. They were divided into several sets because of the numbers of mice bleedings and labor involved but are shown below. Sera are collected as pre-bleed (day 0) and at day 3, 10, and 24 after first immunization, and then at day 38. Sera were allowed to clot centrifuged to separate clot from serum, serum collected and stored individually at −70° C. in labeled tubes (Date, group, and mouse number). Sera were thawed, centrifuged and, if appropriate, pools were prepared from equal amounts of sera from each mouse in the group. Day 24 was boost day, where mice were given the same antigen and dose and test bleed 14 days later for both antibody and cytokines. There were 16 maximum pools per study (A or B), at maximum. There were 8 groups that are the same, all pre-bleeds, as shown in Table 2:

TABLE 2

| STUDY A | STUDY B |
|---|---|
| Group 1 J-NP | Group 1 J-HA2 core 1 |
| Group 2 derG-NP | Group 2 derG HA2 core 1 |

TABLE 2-continued

| STUDY A | STUDY B |
| --- | --- |
| Group 3 J-M2e | Group 3 J-HA2 core 2 |
| Group 4 derG-M2e | Group 4 derG-HA2 core 2 |

FIG. 1 shows a plot of the cytokine response of pooled sera for over 15 select cytokines from sera taken at day 0, 3 and 10 for several groups of mice immunized with J-NP or J-M2e, each with an adjuvant, plus an adjuvant control group and normalized to the adjuvant control for the same bleeding date and strain of mice. The data was obtained using Ray biotech membrane microarray for serum cytokines, chemokines and some related receptors (Taylor et al., Maturation of Dendritic Cell Precursors into IL12 Producing DCs by J-LEAPS Immunogens, Cellular Immunology, 2010; 262(1):1-5). The results show that differences in cytokine responses exist for the different conjugates and strains of mice. For example, higher amounts of MCP-1 and IFN-γ cytokines are shown for BALB/c mice for both J-NP and J-M2e conjugates as compared to (1) IL-12p40, which is higher for C57BL6 mice, (2) or IL-12p70 at day 10 for BALB/c mice, for both J-NP and J-M2e conjugates. In addition as shown FIG. 1, C57BL6 mice had a lower baseline than BALB/c mice for the ratio of antigen plus adjuvant to adjuvant alone for many of the listed cytokines at the times shown.

The study further demonstrated that the conjugates corresponding to SEQ ID NOS. 17-20 were difficult to manufacture and were difficult to purify and stabilize. The derG conjugates of NP and M2e were prepared on several occasions but in some cases not enough soluble usable material was obtained to adequately immunize mice so as to generate an immune response in BALB/c or C57BL6 mice, which was determined by antibodies. Even when the derG conjugates of NP and, especially, of M2e were successfully formulated, the material tended to come out of solution during the time of processing and prior to immunization, which resulted in a clogging of syringes and needles. Therefore, they were nonimmunogenic. Based on the hydrophobicity of derG and the HA2 core 1 and core 2 peptides, a combination was determined unlikely to be possible without modifications. Thus, the successful manufacture and immunization resulting from the J-NP and J-M2e conjugates was remarkable.

It was determined that for primary responses, the NP, M2e, and, especially, the J peptide-containing heterconjugates were more immunogenic in regard to either antibody production (day 24 or 38) or cytokine responses (day 3, 10 and 24). Certainly, no cytokine storm of excessive amounts of proinflammatory or inflammatory cytokines by either Multiplex assay, Luminex or Ray membrane assays were seen in either BALB/c or C57B16 mice for any of the immunogens used, which was the first objective. Since very little response for antibodies or cytokines was seen with the HA2 core 1 or 2 conjugates, KLH conjugates of these peptides were prepared with a highly immunogenic carrier, such as KLH (Keyhole hemocyanin), to show that the H1N1 L.E.A.P.S. (J-HA2 core 1 or 2) peptides could be rendered immunogenic as far as induction of serum antibodies. Regarding the mixtures of H1N1 L.E.A.P.S. conjugates compared to individual H1N1 L.E.A.P.S. conjugates, individual peptides appeared to be more active than mixtures for inducing cytokines from human monocytes.

A secondary response was evaluated on day 38 from sera collected following a secondary immunization (booster) administered on day 24 to Balb/c mice. The secondary immunization was administered in the same manner as the primary immunization, as described above, with either J-NP, J-M2e, J-HA(Core1) and J-HA2(Core2). Day 38 sera from animals immunized (at days 0 and 24) with J-NP or J-M2e (see FIG. 2) showed increased or sustained selected cytokine production. In particular J-M2e showed an increase for IL-12p70, IL-12 p40p70, IFN-y and IL-10, while J-NP showed sustained levels.

Figure 2:
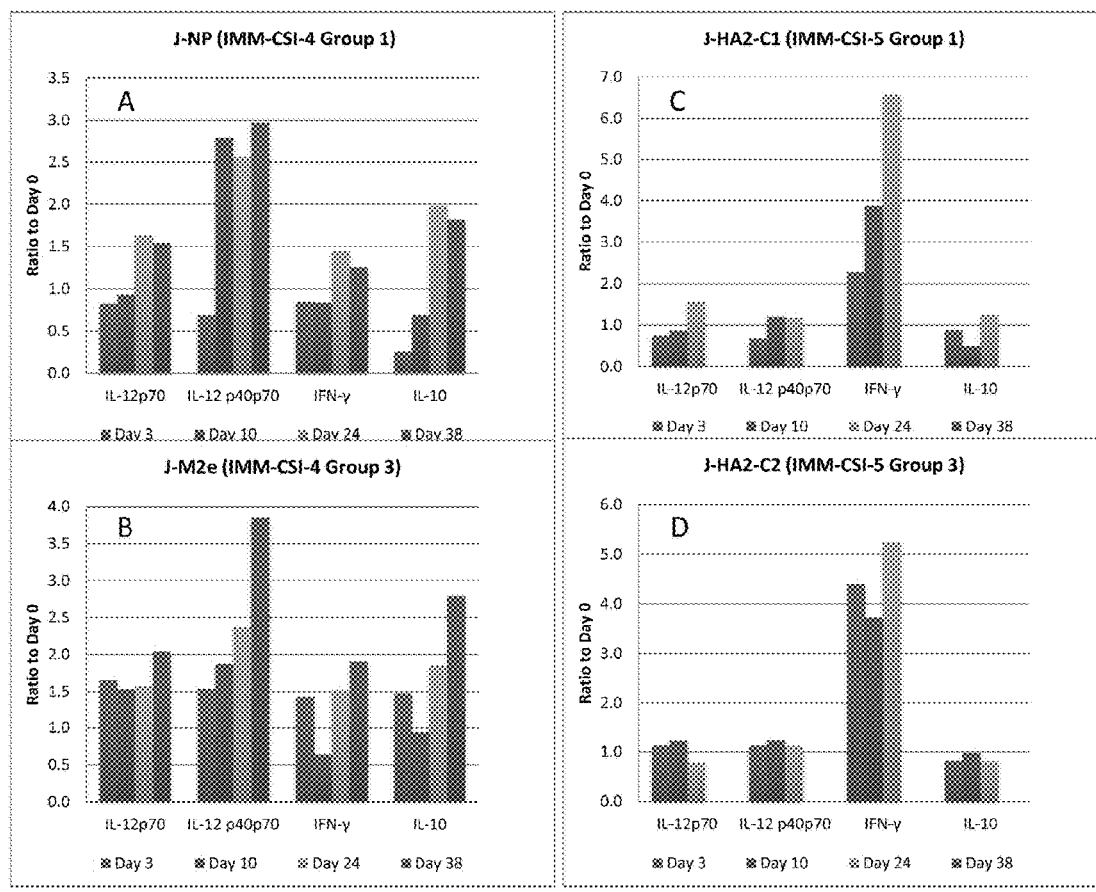
FIG. 2 shows selected cytokine response of pooled sera taken on days 3, 10, 24 and 38 as a ratio to day 0 sera values, in 4 groups of Balb/c mice immunized on day 0 with J-NP, J-M2e, J-HA(Core1) or J-HA2(Core2) and with a secondary immunization on day 24 (booster).

In FIG. 2, a primary immune response at days 3, 10 and 24 is shown for mice immunized with J-NP (FIG. 2A), J-M2e (FIG. 2B), J-HA 1 (FIG. 2C) and J-HA2 (FIG. 2D). A secondary immune response at day 38 is shown for J-NP (FIG. 2A) and J-M2e (FIG. 2B).

EXAMPLE 2

Bone marrow (BM) cells were isolated from Balb/c mice to evaluate the ability of the peptide heteroconjugates disclosed herein to affect a maturation of dendritic cells (DCs). Antigen-presentation cells, including DCs undergo a maturation process when exposed to an antigen of bacterial, viral or other origin to a form capable of interacting with T cells to begin an antigen specific or T cell-mediated immune response. Such DC cells can be referred to as matured, more matured or having undergone maturation from less mature DCs or from precursors to DCs, such as monocytes. BM cells are a good source of obtaining DCs without the presence of T cells. See Inaba K et al 1992 Generation of large numbers of dendritic cells from mouse bone marrow cultures supplemented with agranulocytes macrophage stimulating factor, J. Exp. Med. 176; 1693. Those skilled in the art will understand that DCs and precursors to DCs can also be obtained from blood, spleen or another suitable source. See also Taylor P R, Paustian C A, Koski G K; Zimmerman D H, Rosenthal K S 2010 Maturation of dendritic cell precursors into IL12 producing DCs by J-LEAPS Cellular Immunology 262:1-5 PMC 20163792; Taylor P R, Koski G K, Paustian C A, Cohen P A, Moore F B-G, Zimmerman D S, Rosenthal K S 2010 J-L.E.A.P.S.™ Vaccines Initiate Murine Th1 Responses By Activating Dendritic Cells Vaccine 28:5533-42 PMC 20600501; Holda, J H 1992 LPS activation of Bone marrow natural suppressor cells, Cell Immunol. 141:518.

Instruments were sanitized in 70% alcohol before and between uses. Animals were euthanized and an opening was cut down the thigh of the leg of each animal and the skin opened with scissors, a scalpel, or a razor blade, and skin, muscle and connective tissue peeled aside to access the knee and hip joints. Using a pair of forceps, the femur and tibia were separated from the rest of the tissue by removing the femur and tibia from the hip socket and ankle joints using sterile gauze. The removed femurs were kept in cold RPMI (Rosewell Park Memorial Institute) media while further animals were processed.

Muscle and other tissue were substantially removed from the femur and tibia and cleaned in a 60 mm dish with cold 1×RPMI media and then transferred to a fresh dish with cold RPMI and cleaned a second time. Using a scalpel, each end (epiphyses) of the bones was clipped off. Then, using a 0.22 gauge syringe, each femur or tibia was flushed with 2 mL cold of RPMI media. Cells obtained from 3-4 animals were pooled in a 50 mL tube. The epiphyses collected from each animal were minced in a separate dish and resuspended together with the marrow plugs from the bone shafts.

Culturing the Cells (Example 2)

The collected cells were passed through a 70 μm strainer to remove large debris. Then, the cells suspended in a tube were centrifuged for 10 min. @ 300×g under chilled conditions and the supernatant decanted The cells were resuspended in 1 mL of Red Blood Cell Lysing Buffer and gently mixed for 1 min., followed by adding 10-20 mL of RPMI media. The resuspended cells were then passed through a 70 μm strainer. The cells were then centrifuged a second time, using the same protocol as above, and resuspended in complete RPMI media containing 20 ng/mL murine granulocyte-macrophage colony-stimulating factor (GM-CSF).

The number of cells were counted cells and the volume was adjusted with complete RPMI media with GM-CSF to achieve a density of $1 \times 10^6$ cells/mL. Cells were seeded into a 24-well plate at 1 mL/well and incubated at 37° C. and 5% $CO_2$.

On day 2, the supernatant from each well was removed and each well along with the walls were gently washed with complete RPMI media and then 1 mL of complete RPMI media containing 20 ng/mL murine GM-CSF was replaced in each well. On day 4, 1 mL of complete RPMI media containing 20 ng/mL murine GM-CSF was added to each well.

On days 6-8, the supernatant from each well was removed and replaced with 0.25 mL of complete RPMI media. Then, 0.75 mL of 4/3× concentrated peptide heteroconjugate stock solution was added to each well; the 4/3× peptide heteroconjugate stock solution was freshly prepared and filtered through a sterile 0.2 micron filter in complete RPMI media. The peptide stock was prepared such that a total amount of 14.5 μmol of one or more peptide heteroconjugates (or 10 μg LPS) in complete RPMI media was added to each well. The peptide stock was prepared from lyophilized peptide heteroconjugate as follows: Peptide heteroconjugate was weighted out and suspended in HBSS to 67× concentration, where 1× concentration is 14.5 μmol/mL, adjusted to pH 7 with 0.1M NaOH and aliquoted to 150 μL per vial, and diluted 1:50 (0.12 mL 67× concentrated peptide conjugate and 5.88 mL complete RPMI media) and filter through a 0.2 μm sterile filter to achieve the necessary 4/3× concentrated peptide heteroconjugate stock solution.

Cells in each well with the peptide conjugate (or LPS) were incubated for a specified time period at 37° C. and 5% $CO_2$ and 100% Relative humidity. Cells were processed for using either procedure "a" or "b" below depending upon volume of cell culture to be processed:

a. Changes in morphology were observed along with pH (with phenol red). Supernatants were transferred into 1.5 mL microcentrifuge tubes and centrifuged for 5 min. @ 10 k RPM, and supernatants then decanted into new tubes. Cell pellets were stored at −70° C. as needed.

b. Cells were transferred to 10 mL centrifuge tubes and centrifuged for 5 min. @ 10 k RPM. Cells were resuspended to a density of $2 \times 10^6$ cells/mL in 1×PBS. 0.5 mL of cell solution is a sufficient amount for inoculation of an individual mouse, although in some studies larger cell amounts may be used.

The above methodology is an exemplary methodology that can be used to isolate BM cells, culture and treat DCs and monocytes in the BM cells with GM-CSF, and mature the DCs with exposure to a peptide heteroconjugate or other antigen. However, those skilled in the art will readily recognize that other culture plates and flasks can be used to culture cells where corresponding changes to cell and media amounts will be required. Table 3 below summarizes the size and volume characteristics of several widely-available culture plates and Table 4 lists similar parameters for widely-available culture flasks. Non-limiting guidance or reagent amounts is given in the notes for Tables 3 and 4.

TABLE 3

Characteristics of Multiple Well Plates
Multiple Well Plate

| Corning Multiple Well Plates | Well Diameter (Bottom - mm) | Approx. Growth Area (cm$^2$) | Total Well Volume (mL) | Working Volume low (mL) | Working Volume high (mL) | Depth at Total Volume (mm) | Depth at Working Volume low (mm) | Depth at Working Volume high (mm) |
|---|---|---|---|---|---|---|---|---|
| 6 well | 34.8 | 9.5 | 16.8 | 1.900 | 2.900 | 17.7 | 2.0 | 3.1 |
| 12 well | 22.1 | 3.8 | 6.9 | 0.760 | 1.140 | 18.2 | 2.0 | 3.0 |
| 24 well | 15.6 | 1.9 | 3.4 | 0.380 | 0.570 | 17.9 | 2.0 | 3.0 |
| 48 well | 11 | 0.95 | 1.6 | 0.190 | 0.285 | 16.8 | 2.0 | 3.0 |
| 96 well Flat bottom | 6.4 | 0.32 | 0.36 | 0.100 | 0.200 | 11.3 | 3.1 | 6.3 |

(Single Well Only)

TABLE 4

Characteristics of Cell Culture Flasks
Flasks

| Corning Flasks | Approx. Growth Area (cm$^2$) | Type | Approx. Total Flask Volume (mL) | Recommended Medium Volume low (mL) | Recommended Medium Volume high (mL) | Depth at Total Volume | Depth at Working Volume low (mm) | Depth at Working Volume high (mm) |
|---|---|---|---|---|---|---|---|---|
| T-25 | 25 | triangular | 50 | 5.0 | 7.5 | 20.0 | 2.0 | 3.0 |
|  |  | rectangular | 70 |  |  | 28.0 |  |  |
| T-75 | 75 | rectangular | 290 | 15.0 | 22.5 | 38.7 | 2.0 | 3.0 |
|  |  | triangular | 300 |  |  | 40.0 |  |  |

TABLE 4-continued

Characteristics of Cell Culture Flasks
Flasks

| Corning Flasks | Approx. Growth Area (cm$^2$) | Approx. Total Flask Volume | | Recommended Medium Volume | | Depth at | Depth at Working Volume | |
|---|---|---|---|---|---|---|---|---|
| | | Type | (mL) | low (mL) | high (mL) | Total Volume | low (mm) | high (mm) |
| T-175 | 175 | N/A | 790 | 35.0 | 52.5 | 45.1 | 2.0 | 3.0 |
| T-225 | 225 | rectangular traditional | 900 1000 | 45.0 | 67.5 | 40.0 44.4 | 2.0 | 3.0 |

Notes:
Assuming $1.0 \times 10^5$ cells/cm$^2$ as attached monolayers in culture.
Recommended volume of 0.2-0.3 mL medium per 1 cm$^2$.
Listed numbers as per Corning reference below. Actual flask measurements on Falcon flasks.
[1] Not available for measurement.
[2] Minimum volume recommended at 1.5 mL to minimized evaporation.
Corning. (2008) Surface Areas and Recommended Medium Volumes for Corning Cell Culture Vessels.

The determination of cell counts and/or cell density was performed as follows. Cells were resuspended in media or sterile 1×HBSS. Cells were then diluted 1:10 in 0.4% Trypan Blue and 10 µL of the diluted cells into hemocytometer. The cells were counted in each quadrant and an average calculated. If density exceeded 100 cells per quadrant, the cells were diluted further and reloaded into the hemocytometer. The total cell count was calculated according to Equation (1) as follows:

$$C \times V \times Df \times L = T$$

Where C=Cell count average, V=Volume (µL) of cells, Df=Dilution factor of cells into Trypan Blue, L=Volume (µL) of cells loaded into the hemocytometer, and T=Total cell count.

Maturation of DCs (Example 2)

As discussed, DCs obtained from BM cells or other sources can be matured in the presence of a heteroconjugate peptide as described herein. Maturation can be observed by the presence of increased cytokines in the culture containing the matured DCs. Such matured DCs that have been exposed to a peptide heteroconjugate ex vivo can then be mixed with autologous T cells isolated from the subject and administered to the subject or such matured DCs can be administered directly to the subject to induce an immune response. In the alternative, administration can also be given to a compatible subject.

Table 5 shows the ability of certain heteroconjugates to mature DCs in an ex vivo fashion. Table 5 presents 3 control samples: "MNC" indicates media alone with no cells, "Media" indicates media alone with no supplements to induce maturation and "LPS" indicates cell media containing 10 µg/mL of lipopolysaccharide (LPS) as a positive control, which is a potent immune cell stimulator containing lipid A. As shown in Table 5, levels of TNF-α and IL-12 (or IL-12p70) were measured in triplicate using ELISA kits from different vendors, PeproTech (Rocky Hill, N.J.), R&D Systems (Minneapolis, Minn.) and RayBiotech (Norcross, Ga.). Supernatants were collected after 24 hours (T1), 48 hours (T2), and 72 hours (T3), and analyzed using the ELISA kits as shown in Table 5.

In Table 5, a clear difference in cytokine levels is evident between the two negative controls of "MNC" and "Media" and samples treated with a L.E.A.P.S. protein heteroconjugate. Heteroconjugate used to evaluate cytokine production include Cel-2000 (SEQ ID NO. 34), described above, and JH, which is heteroconjugate peptide vaccine containing the peptide J (SEQ ID No. 3) ICBL conjugated to a peptide "HGP-30" (H) peptide from the p17 HIV gag protein YSVHQRIDVKDTKEALEKIEEEQNKSKKKA (aa 85-115) (SEQ ID NO. 35) through a triglycine linker. As such, the JH heteroconjugate peptide has the sequence DLLKNGERIEKVEGGGYSVHQRIDVKDTKEALE-KIEEEQNKSKKKA (SEQ ID No. 36) with a GGG divalent linker. Differences seen in the sensitivity of the kits is most likely due differences in specificities of the monoclonal antibodies reagents used by different manufacturers. However, differences between the samples treated with a heteroconjugate and those in the negative control groups ("MNC" and "Media") are visible. Further, Table 5 shows that 24 hours is a sufficient amount of time to observe significant maturation of DCs.

TABLE 5

Cytokine Profiles of Dendritic Cells Treated with Heteroconjugates
LCC-6 - TNF-a and IL-12 ELISAs. Results Pools by Sample Type

| | | TNF-a | | | | | | IL-12 | | | |
|---|---|---|---|---|---|---|---|---|---|---|---|
| | | PeproTech TNF-a TNF-a Conc. (pg/mL) | | R&D Systems TNF-a TNF-a Conc. (pg/mL) | | RayBio TNF-a TNF-a Conc. (pg/mL) | | PeproTech (Total IL-12) Total IL-12 Conc. (pg/mL) | | R&D Systems (IL-12p70) IL-12p70 Conc. (pg/mL) | |
| Sample | Treatment Day | Avg | SD | Avg | SD | Avg | SD | Avg | SD | Avg | SD |
| MNC | T1 | — | — | 11.1 | — | — | — | — | — | 13.9 | 0.1 |
| Media | T1 | — | — | 22.6 | 1.5 | — | — | — | — | 15.1 | 3.4 |
| | T2 | — | — | 22.6 | 6.8 | — | — | — | — | 6.0 | 0.7 |
| | T3 | — | — | 29.4 | 23.5 | — | — | — | — | 16.1 | 0.1 |

TABLE 5-continued

Cytokine Profiles of Dendritic Cells Treated with Heteroconjugates
LCC-6 - TNF-a and IL-12 ELISAs. Results Pools by Sample Type

|  |  | TNF-a | | | | | | IL-12 | | | |
|---|---|---|---|---|---|---|---|---|---|---|---|
|  |  | PeproTech TNF-a TNF-a Conc. (pg/mL) | | R&D Systems TNF-a TNF-a Conc. (pg/mL) | | RayBio TNF-a TNF-a Conc. (pg/mL) | | PeproTech (Total IL-12) Total IL-12 Conc. (pg/mL) | | R&D Systems (IL-12p70) IL-12p70 Conc. (pg/mL) | |
| Sample | Treatment Day | Avg | SD | Avg | SD | Avg | SD | Avg | SD | Avg | SD |
| LPS | T1 | 662.1 | 121.8 | 5229.9 | 90.6 | 3206.0 | 71.2 | 1682.7 | 255.5 | 57.0 | 8.2 |
|  | T2 | 389.0 | 16.9 | 3313.2 | 334.3 | 2142.3 | 3.3 | 1818.3 | 861.9 | 78.5 | 5.4 |
|  | T3 | 290.7 | 8.9 | 3083.0 | 114.3 | 2028.6 | 291.8 | 270.9 | 40.4 | 62.5 | 2.3 |
| JH | T1 | 202.5 | 68.2 | 905.7 | 24.2 | 29.6 | 2.0 | 1028.7 | 136.2 | 21.9 | 2.2 |
|  | T2 | 56.1 | 26.6 | 685.0 | 3.7 | — | — | 1080.5 | 497.1 | 40.2 | 1.1 |
|  | T3 | 91.3 | 21.8 | 830.9 | 40.4 | — | — | 183.2 | 40.5 | 11.9 | 0.2 |
| CEL-2000 | T1 | 576.4 | 115.3 | 4561.1 | 197.5 | 3171.6 | 133.3 | 1345.9 | 220.8 | 67.9 | 0.9 |
|  | T2 | 281.0 | 6.2 | 2845.9 | 212.5 | 1343.5 | 12.3 | 401.1 | 179.8 | 35.4 | 1.2 |
|  | T3 | 244.6 | 16.3 | 2022.6 | 199.1 | 722.0 | 16.2 | 316.4 | 19.9 | 58.2 | 1.1 |

It is intended that the present invention include all modifications and improvements known to those of ordinary skill within the scope of the disclosure.

I claim:

1. A peptide heteroconjugate, comprising: a peptide construct consisting of a sequence selected from the group consisting of SEQ ID Nos. 1-2 and 15-32 or a variant thereof; wherein the variant is selected from the group consisting of:
   i) modification to either or both of an N- or C-terminal of the sequence by any one or more of amidation or acylation;
   ii) deletion of 1, 2, 3, 4, or 5 amino acids from the sequence;
   iii) addition of 1, 2, 3, 4, or 5 amino acids to the sequence; and
   iv) substitution of 1, 2, 3, 4 or 5 amino acids in the sequence,
   wherein the peptide construct comprises a sequence of amino acids selected from the group of SEQ ID Nos. 7-10, wherein SEQ ID Nos. 7-10 is an antigen from an influenza virus.

2. The peptide heteroconjugate of claim 1, wherein the peptide construct elicits a stronger primary immune response in a mammal relative to a peptide consisting of SEQ ID Nos. 7-10.

3. The peptide heteroconjugate of claim 1, wherein the mammal is a human.

4. The peptide heteroconjugate of claim 1, further comprising an adjuvant, wherein the adjuvant can optionally be a water-in-oil or water-in-oil-in-water formulation.

5. The peptide heteroconjugate of claim 1, wherein more than one peptide constructs selected from the group consisting of SEQ ID Nos. 1-2 and 15-32 are combined to form a mixture of peptide heteroconjugates.

6. A peptide heteroconjugate, comprising a peptide construct consisting of the formula $P_1$-x-$P_2$ or $P_2$-x-$P_1$, wherein $P_1$ represents a specific antigenic peptide originating from an influenza virus and competent for recognition by a class or subclass of immune cells or binding to an antibody;

$P_2$ represents an immunomodulatory peptide which is a portion of an immunoprotein capable of promoting binding to a class or subclass of immune cells and directing a subsequent immune response to the peptide $P_1$; and x represents a covalent bond or a divalent linking group, wherein $P_2$ is a peptide sequence selected from SEQ ID Nos. 3 and 6 or a variant thereof;

wherein the variant is selected from the group consisting of:

i) modification to either or both of an N- or C-terminal of the sequence by any one or more of amidation or acylation;

ii) deletion of 1, 2, 3, 4, or 5 amino acids from the sequence;

iii) addition of 1, 2, 3, 4, or 5 amino acids to the sequence; and iv) substitution of 1, 2, 3, 4 or 5 amino acids in the sequence, wherein the peptide construct comprises a sequence of amino acids selected from the group of SEQ ID Nos. 7-10, wherein SEQ ID Nos. 7-10 is an antigen from an influenza virus.

7. A vaccine for immunization of a mammal against Type A influenza virus comprising an immunologically effective amount of a peptide heteroconjugate(s) consisting of a sequence selected from the group consisting of SEQ ID Nos. 1-2 and 15-32 or a variant thereof, optionally in combination with an adjuvant;

wherein the variant is selected from the group consisting of:

i) modification to either or both of an N- or C-terminal of the sequence by any one or more of amidation or acylation;

ii) deletion of 1, 2, 3, 4, or 5 amino acids from the sequence;

iii) addition of 1, 2, 3, 4, or 5 amino acids to the sequence; and iv) substitution of 1, 2, 3, 4 or 5 amino acids in the sequence, wherein the peptide construct comprises a sequence of amino acids selected from the group of SEQ ID Nos. 7-10, wherein SEQ ID Nos. 7-10 is an antigen from an influenza virus.

8. The vaccine of claim 7 wherein the vaccine comprises the peptide heteroconjugate(s) in combination with the adjuvant; and wherein the adjuvant is a water-in-oil or water-in-oil-in-water formulation.

9. A therapeutic method, comprising administering an immunologically effective amount of a peptide heteroconjugate consisting of a sequence selected from the group consisting of SEQ ID Nos. 1-2 and 15-32 or variants thereof, optionally with an adjuvant;
   wherein the variant is selected from the group consisting of:
   i) modification to either or both of an N- or C-terminal of the sequence by any one or more of amidation or acylation;
   ii) deletion of 1, 2, 3, 4, or 5 amino acids from the sequence;
   iii) addition of 1, 2, 3, 4, or 5 amino acids to the sequence; and
   iv) substitution of 1, 2, 3, 4 or 5 amino acids in the sequence,
   wherein the peptide construct comprises a sequence of amino acids selected from the group of SEQ ID Nos. 7-10, wherein SEQ ID Nos. 7-10 is an antigen from an influenza virus.

10. The method of claim 9, wherein said peptide heteroconjugate is administered as a single dose.

11. The method of claim 9, comprising the additional step of administering one or more subsequent booster doses.

12. The method of claim 9, wherein the adjuvant is a water-in-oil or water-in-oil-in-water formulation.

13. The method of claim 9, wherein the immune response is a primary immune response.

14. A method for modulating a response to Type A influenza virus in a subject in need thereof, comprising:
   combining precursors of dendritic cells taken from the blood, bone marrow, spleen, or other suitable source with a peptide heteroconjugate(s) consisting of a sequence selected from the group consisting of SEQ ID Nos. 1-2 and 15-32 or a variant thereof ex vivo to form a mixture, and incubating from one hour to several days to allow maturation to form more mature dendritic cells, and
   administering the mixture to the same subject from which the precursors of dendritic cells were taken or to a genetically compatible subject;
   wherein the variant is selected from the group consisting of:
   i) modification to either or both of an N- or C-terminal of the sequence by any one or more of amidation or acylation;
   ii) deletion of 1, 2, 3, 4, or 5 amino acids from the sequence;
   iii) addition of 1, 2, 3, 4, or 5 amino acids to the sequence; and
   iv) substitution of 1, 2, 3, 4 or 5 amino acids in the sequence,
   wherein the peptide construct comprises a sequence of amino acids selected from the group of SEQ ID Nos. 7-10, wherein SEQ ID Nos. 7-10 is an antigen from an influenza virus.

15. The method of claim 14, wherein the mixture is administered to the subject after the mixing step.

16. The method of claim 14, wherein the mixture is administered to the subject after ex vivo incubation in cell culture.

17. The method of claim 14, wherein the more matured dendritic cells produce higher amounts of IL-12 than the precursors of dendritic cells taken from blood, bone marrow, spleen, or other suitable source.

18. The method of claim 14, further comprising administering the mixture to the subject with supplementary immunomodulators.

* * * * *